US007150888B1

(12) United States Patent
Vail, III et al.

(10) Patent No.: US 7,150,888 B1
(45) Date of Patent: *Dec. 19, 2006

(54) METHODS AND APPARATUS TO PREVENT COLDS, INFLUENZAES, TUBERCULOSIS AND OPPORTUNISTIC INFECTIONS OF THE HUMAN RESPIRATORY SYSTEM

(75) Inventors: William Banning Vail, III, Bothell, WA (US); Marilyn L. Vail, Bothell, WA (US)

(73) Assignee: Inhalation, Inc., Woodinville, WA (US)

( * ) Notice: Subject to any disclaimer, the term of this patent is extended or adjusted under 35 U.S.C. 154(b) by 661 days.

This patent is subject to a terminal disclaimer.

(21) Appl. No.: 10/241,441

(22) Filed: Sep. 9, 2002

Related U.S. Application Data

(63) Continuation-in-part of application No. 09/542,703, filed on Apr. 3, 2000, now Pat. No. 6,447,816.

(60) Provisional application No. 60/328,912, filed on Oct. 12, 2001, provisional application No. 60/377,177, filed on May 2, 2002.

(51) Int. Cl.
*A61K 35/78* (2006.01)
*A61K 51/00* (2006.01)
*A01N 25/00* (2006.01)

(52) U.S. Cl. ............... 424/742; 424/404; 424/1.13; 514/924

(58) Field of Classification Search ............... 424/742, 424/404; 514/959, 957, 924
See application file for complete search history.

(56) References Cited

U.S. PATENT DOCUMENTS

| 4,523,589 | A | 6/1985 | Krauser |
|---|---|---|---|
| 4,955,945 | A | 9/1990 | Weick |
| 5,175,152 | A | 12/1992 | Singh |
| 5,511,726 | A | 4/1996 | Greenspan et al. |
| 5,578,338 | A | 11/1996 | Shimabukuro |
| 5,666,946 | A | 9/1997 | Langenback |
| 6,207,703 | B1 | 3/2001 | Ponikau |
| 6,291,500 | B1 | 9/2001 | Ponikau |
| 6,416,955 | B1 | 7/2002 | Sherris et al. |
| 6,447,816 | B1 | 9/2002 | Vail, III et al. |
| 6,550,474 | B1 | 4/2003 | Anderson et al. |
| 6,555,566 | B1 | 4/2003 | Ponikau |
| 2001/0002400 | A1 | 5/2001 | Ponikau |
| 2001/0006944 | A1 | 7/2001 | Ponikau |
| 2001/0031779 | A1 | 10/2001 | Ponikau |
| 2002/0052390 | A1 | 5/2002 | Ponikau |
| 2002/0189608 | A1 | 12/2002 | Raudenbush |
| 2003/0086991 | A1 | 5/2003 | Hughes et al. |
| 2003/0087848 | A1 | 5/2003 | Bratzler et al. |
| 2003/0098022 | A1 | 5/2003 | Nakao et al. |

FOREIGN PATENT DOCUMENTS

| DE | 296 20 182 U1 | 5/1997 |
|---|---|---|
| JP | 11-209265 | 8/1999 |
| WO | WO 00/65341 | 11/2000 |
| WO | WO 01/60395 A2 | 8/2001 |
| WO | WO 03/037412 A2 | 5/2003 |

OTHER PUBLICATIONS

Audesirk et al., "Biology, Life on Earth", Fourth Edition, pp. 427-429, and 522-523, Prentice Hall, Upper Saddle River, NJ, 1996.

Balch et al., "Prescription for Nutritional Healing", Second Edition, pp. 69, 77, 167-169, 209-211, 277, 346-348 and 428-430, Avery Publishing Group, Garden City Park, NY, 1997.

Fugh-Berman, "Alternative Medicine, What Works", pp. 3-16, and 192-194, Williams & Wilkins, Baltimore, MD, 1997.

Hans Dieter Knoch, "Tea Tree Export—Typical Analysis", pp. 1-3, ttexport@nrg.com.au, Mar. 9, 2000.

Hawken, "Natural Cold and Flu Defense", pp. 5-30, Woodland Publishing, Pleasant Grove, UT, 1997.

Hodges et al., "Component Analysis of Eucalyptus Oil by Gas Chromatography-Fourier Transform-Infrared Spectrometry-Mass Spectrometry", Journal of Chromatographic Science, pp. 345-350, vol. 29(8), Aug. 1991.

Hoffmann, "The Herbal Handbook", p. 95, Healing Arts Press, Rochester, VT, 1998.

Hoffmann, "The Complete Illustrated Holistic Herbal", pp. 184-187, Element Books, Inc., 1996.

Igram, "Killed on Contact, The Tea Tree Oil Story: Nature's Finest Antiseptic", pp. 1-18, and 51-61, Literary Visions Publishing, Inc., Cedar Rapids, IA, 1992.

Kohn et al., "To Err Is Human, Building a Safer Health System, Advance Copy", pp. 1-14, Institute for Medicine, National Academy Press, Washington D.C., 1999.

Lawless, "Tea Tree Oil", pp. 3-29 and 111-114, Harper Collins Publishers, Hammersmith, London U.K., 1994.

Lawless, "The Illustrated Encyclopedia of Essential Oils", pp. 139-141, Barnes & Noble Books, New York, NY, 1999.

Luckmann, "Saunders, Manual of Nursing Care", pp. 921-929, W.B. Saunders Company, Philadelphia, PA, 1997.

Martin et al., "A Dictionary of Biology", Third Edition, p. 31, Oxford University Press, New York, NY, 1996.

Miller et al., "Ayurveda & Aromatherapy, The Earth Essential Guide to Ancient Wisdom and Modern Healing", pp. 251-252, Lotus Press, Twin Lakes, WI, 1995.

Murray et al., "An Encyclopedia of Natural Medicine", pp. 227-231, Prima Publishing, Rocklin, CA, 1991.

(Continued)

*Primary Examiner*—Michele Flood

(57) ABSTRACT

Strong vapors from eucalyptus oil and tea tree oil are inhaled periodically to prevent respiratory system diseases including colds, flus, pneumonia, tuberculosis, and opportunistic infections in individuals having cystic fibrosis. Apparatus for the periodic inhalation of strong vapors from eucalyptus oil and tea tree oil are provided.

1 Claim, 1 Drawing Sheet

OTHER PUBLICATIONS

Olsen, "Australian Tea Tree Oil Guide", pp. 14-16, Kali Press, Pagosa Springs, CO, 1991.

Olsen, "Australian Tea Tree Oil Guide", Third Edition, pp. 10-13, and 82-84, Kali Press, Pagosa Springs, CO, 1997.

Roberts et al., "Asthma: An Alternative Approach", pp. 133-137, Keats Publishing, Inc., New Canaan, CT, 1997.

Rose, "375 Essential Oils and Hydrosols", pp. 77-78, Frog Limited, Berkeley, CA, 1999.

Schnaubelt, "Advanced Aromatherapy, The Science of Essential Oil Therapy", pp. 31-41, and 96-124, Healing Arts Press, Rochester VT, 1998.

Swords et al., "Composition of Australian Tea Tree Oil (Melaleuca alternifolia)", pp. 734-737, Journal of Agricultural Food Chemistry, vol. 26, No. 3, 1978.

Tenney, "Aromatherapy Essential Oils for Essential Health", pp. 5-26, Woodland Publishing, Pleasant Grove, UT, 1997.

The Seattle Times, "Medical Digest—Protein could beat cholesterol as indicator of heart risk", Friday, Mar. 24, 2000.

Weinstein, "Asthma, The Complete Guide to Self-Management of Asthma and Allergies for Patients and Their Families", pp. 1-357, A Fawcett Crest Book, The Ballantine Publishing Group, New York, NY, 1988.

Williams, "New Uses for An Age-Old Therapy", pp. 25-27, Alternatives For the Health Conscious Individual, vol. 8, No. 4, Oct. 1999.

Anderson, "Mosby's Medical Dictionary", Fourth Edition, pp. 1476-1477, Mosby-Year Book, Inc., St. Louis, MO, 1994.

McGuffin et. al., "American Herbal Products Association's Botanical Safety Handbook", pp. 155-157, CRC Press, New York, NY, 1997.

Paterson et. al., "Reduced susceptibility of Staphylococcus aureus to vancomycin—a review of current knowledge" pp. 1-6, Communicable Disease Intelligence, vol. 23 No. 3, Apr. 20, 1999.

Sherry et. al., "Alternative for MRSA and Tuberculosis (TB): Eucalyptus and Tea-Tree Oils as New Topical Antibacterials", 2002 Annual Meeting of the American Academy of Orthopaedic Surgeons, Feb. 13-17, 2002, Dallas, TX, Poster Board No. P376.

Blumenthal et al., The Complete German Commission E Monographs: Therapeutic Guide to Herbal Medicines, p 267, "Fixed combinations of eucalyptus oil and pine needle oil, published Jul. 14, 1993", American Botanical Council, USA, 1998.

Carson et al., J. of Applied Bacteriology (1995), 78:264-269, "Antimicrobial activity of the major components of the essential oil of Melaleuca alternifolia".

Carson et al., J. Antimicrobial Chemotherapy (1995), 35:421-424, "Susceptibility of methicillin-resistant Staphyloccus aureus to the essential oil of Melaleuca alternifolia".

Balch et al., Prescription for Nutritional Healing, Second Edition, p. 144, pp. 167-168, Avery Publishing Group, Garden City Park, NY, 1997.

Hoffmann, The Complete Illustrated Herbal, pp. 184-185, Barnes & Noble Books, 1999.

Grant, "Prolific Bothell inventor tackles common cold with latest creation", pp. D1 and D6, Eastside Journal, Sep. 14, 2002.

Dietrich, "Vapor inhaler gives inventor a mist opportunity", p. 16, Puget Sound Business Journal, Feb. 21-27, 2003.

Berkow et al., "The Merck Manual of Medical Information, Home Edition". pp. 1015-1017, Pocket Books, a division of Simon & Schuster, Inc., New York, NY, 1997.

Beers et al., "The Merck Manual of Diagnosis and Therapy", Seventeenth Edition, Centennial Edition, Home, Section 7, Chapter 86, "Sinusitis", 1999.

Allergy, Asthma, and Sinus Resource Center, "Allergy & Sinus Relief Without Drugs", www.allergy-asthma-sinus.com, Apr. 30, 2002.

Medical College of Wisconsin Physicians & Clinics, "Sinusitis (Sinus Infection)", Health Link, Apr. 30, 2002.

"Sinusitis", Medical Encyclopedia, drkoop.com, Apr. 30, 2002.

Beers et al., "The Merck Mannual of Diagnosis and Therapy" Seventeenth Edition, Centennial Edition, Home, Section 13, Chapter 157, "Caused By Mycobacteria-Tuberculosis", 1999.

Balch et al., "Prescription for Nutritional Healing", Third Edition, pp. 311-313, Avery Publishing Group, Garden City Park, NY, 2000.

Beers et al, "The Merck Manual of Diagnosis and Therapy" Seventeenth Edition, Centennial Edition, Home Section 19, Chapter 267, "Cystic Fibrosis", 1999.

Balch et al., "Prescription for Nutritional Healing", Third Edition, pp. 567-569, Avery Publishing Group, Garden City Park, NY, 2000.

Beers et al., "The Merck Manual of Diagnosis and Therapy" Seventeenth Edition, Centennial Edition, Home, Section 6, Chapter 73, "Pneumonia", 1999.

Balch et al., "Prescription for Nutritional Healing", Third Edition, pp. 297-300, 468-470, Avery Publishing Group, Garden City Park, NY, 2000.

Beers et al., "The Manuel of Diagnosis and Therapy" Seventeenth Edition, Centennial Edition, Home, Section 13, Chapter 162, "Respiratory Viral Diseases", 1999.

"Common Infections", www.cohis.org, Apr. 30, 2002.

Beers et al., "The Merck Manual of Diagnosis and Therapy" Seventeenth Edition, Centennial Edition, Home, Section 7, Chapter 86, "Rhinitis", 1999.

Balch et al., "Prescription for Nutritional Healing", Third Edition, pp. 195-200, Avery Publishing Group, Garden City Park, NY, 2000.

Berkow et al., "The Merck Manual of Medical Information, Home Edition", pp. 173-180, Pocket Books, a division of Simon & Schuster, Inc., New York, NY, 1997.

Beers et al., "The Merck Manual of Diagnosis and Therapy" Seventeenth Edition, Home, Section 6, Chapter 68, "Chronic Obstructive Airway Disorders", 1999.

Price et al., "Aromatherapy for Health Professionals", pp. 59-87, Churchill Livingstone, New York, NY, 2000.

Inouye et al., "Antibacterial activity of essential oils and their major constituents against respiratory tract pathogens by gaseous contact", Journal of Antimicrobial Chemotherapy, vol. 47, 565-573, 2001.

Zakarya et al., "Chemical Composition-Antimicrobial Activity Relationships of Eucalyptus Essential Oils", Plantes medicinales et phytotherapie, vol. XXVI, No. 4, pp. 319-331.

Maruzzella et al., "The Action of Perfume Oil Vapors on Fungi", American Perfumer and Aromatics, vol. 73, Jan.-Jun. 1959, pp. 21-22.

Maruzzella et al., "Antibacterial Activity of Essential Oil Vapors", Journal of the American Pharmaceutical Association, vol. 49, No. 11, Nov. 1960, pp. 692-694.

Boyd et al., "Nutmeg Oil and Camphene as Inhaled Expectorants", Archives of Otolaryngology, vol. 92, No. 4, Oct. 1970, pp. 372-378.

Megalla et al., "A Study of Antimicrobial Action of Some Essential Oil Constituents", Herba Polonica, vol. XXVI, No. 3, 1980, pp. 181-186.

Pandey et al., "Fungitoxic and phytotoxic properties of the essential oil of Hyptis suaveolens", Journal of Plant Diseases and Protection, vol. 89 No. 6, 1982, pp. 344-349.

Burrow et al., "The Effects of Camphor, Eucalyptus and Menthol Vapour on Nasal Resistance to Airflow and Nasal Sensation", Acta Oto-Laryngologica, vol. 96, No. 1-2, Jul.-Aug. 1983, pp. 157-161.

Inouye et al., "Inhibitory Effect of Volatile Constituents of Plants on the Proliferation of Bacteria—Antibacterial Activity of Plant Volatiles—", Journal of Antibacterial Antifungal Agents, vol. 11, No. 11, 1983, pp. 609-615.

Goi et al., "Antifungal Activity of Powdery Black Mustard, Powdery Wasai (Japanese Horseradish), and Allyl Isothiocyanate by Gaseous Contact—Antifungal Activity of Plant Volatiles—", Journal of Antibacterial Antifungal Agents, vol. 13, No. 5, 1985, pp. 199-204.

Onawunmi et al., "Effects of lemon grass oil on the cells and spheroplasts of Escherichia coli NCTC 9001", Microbios Letters, vol. 28 No. 110, 1985, pp. 63-68.

Moleyar et al., "Antifungal activity of some essential oil components", Food Microbiology, vol. 3 No. 4, Oct. 1986, pp. 331-336.

Knobloch et al., "Antibacterial and Antifungal Properties of Essential Oil Components", Jounal of Essential Oil Research, vol. 1 No. 3, May/Jun. 1989, pp. 119-128.

Farag et al., "Antimicrobial Activity of Some Egyptian Spice Essential Oils", Journal of Food Protection, vol. 52 No. 9, Sep. 1989, pp. 665-667.

Gocho, "Antibacterial Action of Aroma Compounds in Vapor State", Journal of Antibacterial Antifungal Agents, vol. 19, No. 7, 1991, pp. 329-334.

Grosjean et al., "Atmospheric Oxidation of Selected Terpenes and Related Carbonyls: Gas-Phase Carbonyl Products", ES&T, vol. 26 No. 8, Aug. 1992, pp. 1526-1533.

Orafidyiya, "The Effect of Autoxidation of Lemon-grass Oil on its Antibacterial Activity", Phytotherapy Research, vol. 7, 1993, pp. 269-271.

Laude et al., "Antitussive Effects of Menthol, Camphor and Cineole In Conscious Guinea-pigs", Pulmonary Pharmacology, vol. 7, 1994, pp. 179-184.

Tassou et al., "Antimicrobial Activity of the Essential Oil of Mastic Gum (*Pistacia lentiscus* var. chia) on Gram Positive and Gram Negative Bacteria in Broth and in Model Food System", International Biodeterioration & Biodegradation, vol. 36, 1995, pp. 411-420.

Singh et al., "Cinnamon bark oil, a potent fungitoxicant against fungi causing respiratory tract mycoses", Allergy, vol. 50 No. 12, dec. 1995, pp. 995-999.

Smith-Palmer et al., "Antimicrobial properties of plant essential oils and essences against five important food-bome pathogens", Letters in Applied Microbiology, vol. 26 No. 2, feb. 1998, pp. 118-122.

Mann et al., "The outer membrane of *Pseudomonas aeruginosa* NCTC 6749 contributes to its tolerance to the essential oil of *Melaleuca alternifolea* (tea tree oil)", Letters in Applied Microbiology, vol. 30 No. 4, Apr. 2000, pp. 294-297.

Janssen et al., "Antimicrobial Activity of Essential Oils: A 1976-1986 Literature Review. Aspects of the Test Methods", Planta Medica, Journal of Medicinal Plant Research, 1987, pp. 395-398.

Boyd et al., "The Effect of Steam Inhalation of Volatile Oils on the Output and Composition of Respiratory TractFluid", The Journal of Pharmacology and Experimental Therapeutics, vol. 163, No. 1, 1968, pp. 250-256.

Inouye et al., "effect of Sealing and Tween 80 on the Antifungal Susceptibility Testing of Essential Oils", Microbiology and Immunlogy, vol. 45 No. 3, 2001, pp. 201-208.

Inouye et al., "Screening of the Antibacterial effects of a variety of essentials oils on respiratory tract pathogens, using a modifid dilution assay method", Journal of Infection and Chemotherapy, vol. 7, No. 4, dec. 2001.pp. 251-254.

Sherry et al., "Percutaneous treatment of chronic MRSA osteomyelitis with a novel plant-derived antiseptic antiseptic", BMC Surgery, vol. 1, No. 1, 2001, pp. 1-4-Aug. 26, 2003 printout.

Beers et al., "The Merck Manual of Diagnosis and Therapy" Seventeenth Edition, Centennial Edition, Home, Section 6, Chapter 73, "Viral Pneumonia", 1999.

Beers et al., "The Merck Manual of Diagnosis and Therapy" Seventeeth Edition, Centennial Edition, Home, Section 6, Chapter 73, "Pneumonia Caused by, Gram-Negative Bacilli", 1999.

Beers et al., "The Merck Manual of Diagonisis and Therapy" Seventeeth Edition, Centennial Edition, Home Section 6, Chapter 73, "Fungal Pneumonia", 1999.

METHODS AND APPARATUS TO PREVENT COLDS, INFLUENZAES, TUBERCULOSIS AND OPPORTUNISTIC INFECTIONS OF THE HUMAN RESPIRATORY SYSTEM

CROSS-REFERENCES TO RELATED APPLICATIONS

This application is a Continuation-in-Part Application of a pending application that is entitled "Methods and Apparatus to Prevent Colds, Flus, and Infections of the Human Respiratory System", which is Ser. No. 09/542,703, which has a filing date of Apr. 3, 2000, and which is due to issue as U.S. Pat. No. 6,447,816 on the date of Sep. 10, 2002. An entire copy of Ser. No. 09/542,703 is incorporated herein by reference.

This application relates to Provisional Patent Application No. 60/328,912 filed on Oct. 12, 2001 that is entitled "Methods and Apparatus to Prevent Infections of the Human Respiratory System from Inhaled Anthrax, Smallpox, Botulism, Plague, Tularemia, Tuberculosis and Other Inhaled Bioterrorism Pathogens". An entire copy of Provisional Patent Application No. 60/328,912 is incorporated herein by reference.

This application also relates to Provisional Patent Application No. 60/377,177 filed on May 2, 2002 that is entitled "Methods and Apparatus to Prevent, Treat, and Cure Infections of the Human Respiratory System Including the Sinus Cavities, the Nasal Cavities, and the Throat". An entire copy of Provisional Patent Application No. 60/377,177 is incorporated herein by reference.

Applicant claims priority from the above U.S. patent application Ser. No. 09/542,703. Applicant further claims priority from the above Provisional Patent Application No. 60/328,912 and the above Provisional Patent Application No. 60/377,177.

BACKGROUND OF THE INVENTION

One of the inventors has poor respiratory health, has had repeated bouts with pneumonia, colds, flu, asthma, and has been recently diagnosed with the initial stages of emphysema—despite all that modern medicine has had to offer. This first inventor also comes from a family known for a long history of respiratory problems. Therefore, the inventors decided to look beyond conventional "modern medicine" to help the first inventor, and as a result, have conceived methods to substantially prevent colds, flus, and infections of the human respiratory system. These methods include the inhalation of the vapors from eucalyptus oil and/or tea tree oil that are theorized to form a protective, and infection-preventing, thin layer within the entire respiratory system, including the lungs, bronchial tubes, and the nasal cavities. This thin layer maintains its anti-pathogenic properties for a period of time following the inhalation of the vapors for at least one-half hour, and perhaps longer. This thin anti-pathogenic layer substantially prevents the initial infection of colds, flus, and other pathogens for a period of time following inhalation. The inventors also propose the prophylactic use of inhaled eucalyptus oil and/or tea tree oil to prevent additional pathogenic infections such as tuberculosis, which is becoming a major health problem in the United States. The inventors further propose the prophylactic use of inhaled eucalyptus oil and/or tea tree oil to prevent opportunistic infections of the human respiratory system of individuals having cystic fibrosis.

1. Field of the Invention

The field of invention relates to the prevention of colds, flus, and other pathogens within the respiratory system of human beings by the inhalation of vapors from highly volatile essential oils such as eucalyptus oil and/or tea tree oil. Following the inhalation of the vapors, a thin anti-pathogenic layer is formed in the respiratory system that protects against infection for a certain duration of time following inhalation.

2. Description of the Prior Art

While certain medical uses for eucalyptus oil and tea tree oil have been previously disclosed, to the inventor's best knowledge, none of those previously disclosed methods have suggested, or proposed, that the periodic inhalation of vapors from eucalyptus oil and/or tea tree oil may be used as prophylactic agents to substantially prevent infection of colds, flus, and other pathogens within the respiratory system of human beings for a duration of time following that inhalation. AFTER the infection of human beings with certain pathogens, previous inhalation therapies have suggested using eucalyptus oil and or tea tree oil to aid in the recovery from certain respiratory diseases. However, none of these previous methods have suggested using eucalyptus oil and/or tea tree oil vapors as prophylactic agents to routinely and substantially PREVENT the initial infection of pathogens for a duration of time following their inhalation as a primary method of preventing disease.

SUMMARY OF THE INVENTION

An object of the invention is to provide methods to prevent the initial infection of pathogens within the human respiratory system by the inhalation of vapors from eucalyptus oil or from any of its constituents.

Another object of the invention is to provide methods to prevent the initial infection of pathogens within the human respiratory system by the inhalation of vapors from tea tree oil or from any of its constituents.

Yet another object of the invention is to prevent respiratory infections from pathogens including bacteria, viruses, and fungi.

And yet another object of the invention is provide methods to substantially prevent diseases such as colds and flus.

Yet another object of the invention is to provide methods to substantially prevent all varieties of pneumonia.

Yet further, another object of the invention is to provide methods to substantially prevent the spread of tuberculosis.

Yet another object of the invention is to provide methods to substantially prevent opportunistic infections of the human respiratory system of individuals having cystic fibrosis.

And finally, another object of the invention is to provide an inhaler apparatus conveniently made to provide vapors from essential oils such as eucalyptus oil and/or tea tree oil for inhalation into the human respiratory system.

DESCRIPTION OF THE PREFERRED EMBODIMENTS

Figure 1:
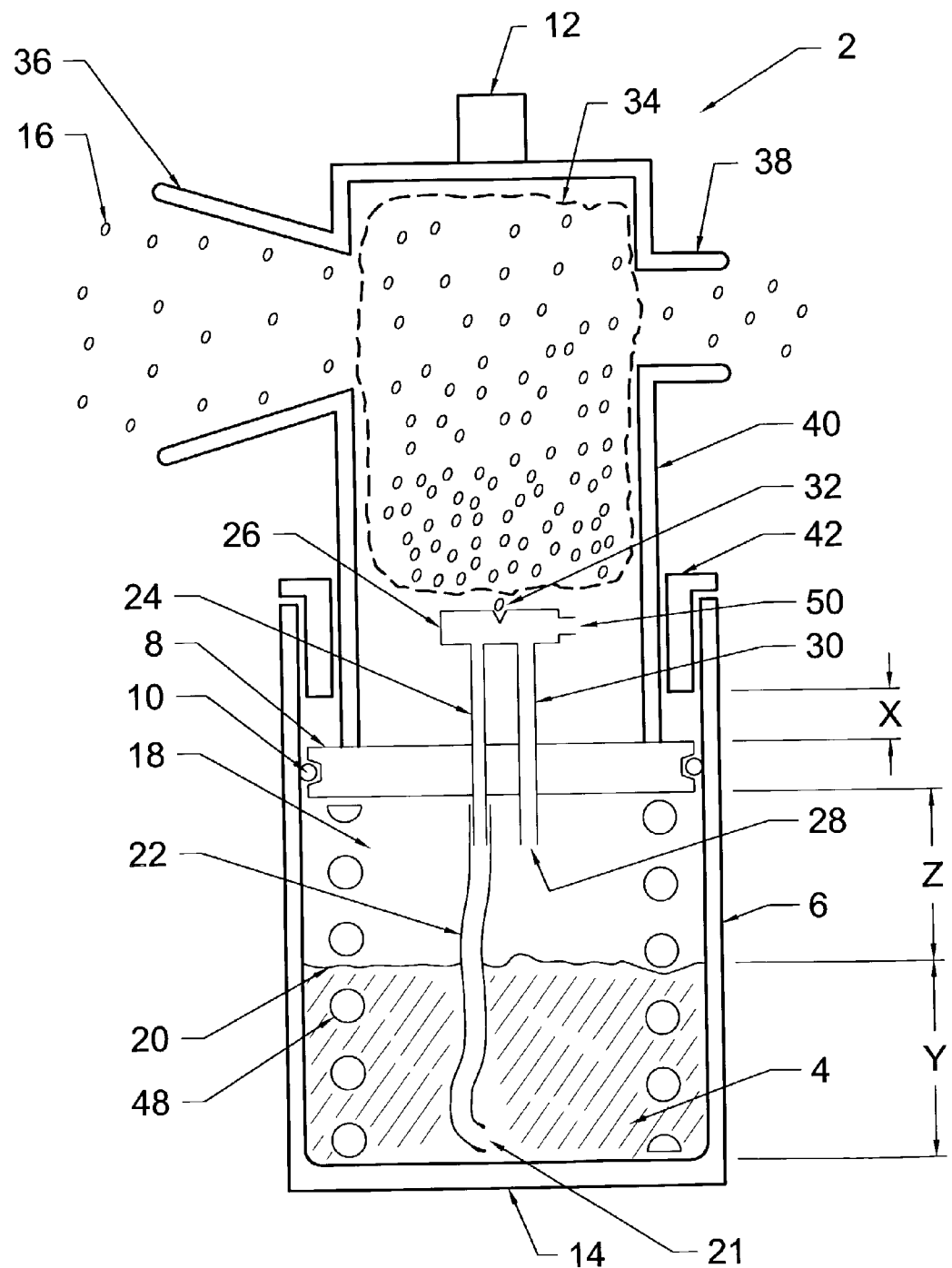
FIG. 1 shows a section view of a hand-held atomizer apparatus to produce vapors from eucalyptus oil and/or tea tree oil for inhalation to prevent pathogens from infecting the human respiratory system.

Following a business trip to Houston during April of 1998, the first inventor, W. Banning Vail, Ph.D., returned to Seattle and caught a dreadful form of flu. During this severe illness, the first inventor spent several weeks gasping for breath and nearly died. After several trips to a pulmonary specialist, it was found that about ⅓ of the first inventor's lung capacity had been "eaten up" by some sort of infectious agent. Therefore, the first inventor was diagnosed with a form of emphysema.

The physician further informed the first inventor that if one more such infectious episode should occur, and should that episode result in another ⅙ or more of the first inventor's lung capacity being "eaten up" by an infectious agent, then the first inventor would thereafter become a good candidate for use of oxygen tanks. Further, the first inventor was also diagnosed with asthma. The physician provided additional warnings of potential disaster in light of the first inventor's many childhood bouts with pneumonia that left scars on the lungs. Such warnings were also compounded by the first inventor's stupid habit of smoking, which he quite some 20 years ago.

The first inventor's father, William Banning Vail, Jr., had emphysema, and had used oxygen tanks for perhaps five years. Accordingly, the first inventor feared emphysema and the use of oxygen tanks. The terms such as "emphysema", "asthma", and related diseases are defined and described in Weinstein, 1988, an entire copy of which is incorporated herein by reference. The clinical manifestations of emphysema, asthma, and other respiratory infections are defined and described in Luckmann, 1997, an entire copy of which is incorporated herein by reference.

For many years, it seems almost every time that the first inventor had taken an airplane flight, or had otherwise gone into a public place with a large number of people, he had often caught a cold, a flu, or some other "bug". The terms such as "cold", "flu", "infectious disease", "pathogen" "pathogens", "pathogenesis", "pathologic microorganisms", etc., are defined in Anderson, et al., 1994, an entire copy of which is incorporated herein by reference. Here, colds include diseases caused by any strain of a rhinovirus. Here, flus include diseases caused by any type of influenza, including those of the respiratory system. Therefore, the first inventor came to fear airplane flights, being in places with many people, etc. because of fear of being infected again with pathogens that could possible result in death by terminal emphysema.

In Anderson, et. al, 1994, on page 808, the term "risk for infection" is defined as "a state in which an individual is at increased risk for being invaded by pathogenic organisms". Anderson, et. al, 1994, page 808, further states: "Risk factors include inadequate primary defenses, such as broken skin, traumatized tissue, decrease in ciliary action . . . , tissue destruction, . . . ".

Luckmann, 1997, page 868, also states under the topic of "Nonspecific Body Defenses Against Infection", and under "1. Physical barriers" the following:

"a. Physical, or anatomic, barriers are the 1st line of defense against infection." and "b. Physical barriers include intact skin and mucous membranes lining the respiratory, gastrointestinal and genitourinary tracts."

Therefore, Luckmann, 1997 specifically refers to the mucous membranes lining the respiratory system as being important to prevent infection, and any less than optimum condition of these membranes would provide another "risk factor" favoring infection by some pathogen.

The first inventor has set forth an hypothesis that his respiratory system and lungs are subject to such "risk factors", and that the first inventor had to invent a new method to prevent invasion by such pathogenic organisms. Consequently, the first inventor has concluded that to minimize the possibility of ending up on oxygen tanks, that it is necessary to prevent the infection of his respiratory system by common pathogens such as pathologic bacteria, viruses, and fungi. It is clear that any one of these pathogens may cause disease. However, the first inventor has the additional hypothesis, that in analogy with many biological systems, it is likely that human diseases can also be caused by a combination of such pathogens that form symbiotic relationships, similar to well-documented mycorrhizal relationships or the like, which may also change in time. For a description of such mechanisms in biology, for example see Audesirk and Audesirk, 1996 on these and related subjects. Therefore, from the first inventor's point of view, it is possible that any one disease may involve bacteria, viruses, and fungi all at one time, and the mix of these may change vs. time as the disease progresses through various stages.

From the first inventor's point of view, many of his illnesses had begun with either cold-like symptoms or flu-like symptoms. If he got very sick, this often progressed into symptoms mimicking those of pneumonia. So, an initial predominant viral-like infection may evolve into a predominantly bacterial-like infection as time progresses. So, the first inventor views the development of some diseases as progression of various stages, where any one stage may have a peculiar mix of pathogens. The progression of colonies of pathogens vs. time may in fact involve viral, bacterial, and fungal elements called for the purposes herein "symbiotic pathogens" that may make "symbiotic pathogenic colonies". Typically, the composition of those "symbiotic pathogenic colonies" vary with time. As has often been the case in the past, when the first inventor had problems with his respiratory system, standard antibiotics rarely helped. In the first inventor's view, this is because the antibiotics only addressed part of the problem in a typically complex case when "symbiotic pathogens" are causing disease that has at least two components among the three that are viral, bacterial, and fungal components. The view that a given disease is often caused by a time varying mix of bacterial, viral, and fungal pathogens provides the precise reason why the first inventor rarely found commercial antibiotics to be of effective help in overcoming his various lung diseases. Accordingly, the first inventor has theorized that to be able to routinely prevent colds, flus, etc., it is necessary to locate substances that have antiviral and antibacterial and antifungal elements that may be applied to the respiratory system simultaneously.

The first inventor further hypothesized that microscopic portions of his respiratory system at any one time are subject to increased risk of invasion by such pathogens. Any such increased risk site for the purposes herein is defined as a "likely pathogenic invasion site". Once a pathogen "invades" such a "likely pathogenic invasion site", for example within tissue within the lungs, then the pathogens may multiply, causing an infection that may "eat away" the lungs of the first inventor. The first inventor has concluded that he needs new methods and apparatus to prevent or block the invasion of pathogens into a likely pathogenic invasion site within his respiratory system. Put another way, the first inventor sought to find a practical method to reduce the risk of infection of the respiratory system by infectious agents.

This is a tall order. The first inventor had theorized about using certain face masks, filtering the air inhaled by the lungs, and passing inhaled air through U.V. light (with the energy of the U.V. below the threshold to produce ozone). Then, the first inventor decided to investigate inhaled chemicals to prevent the invasion by pathogens of a likely pathogenic invasion site. Such chemicals need to be highly volatile, non-toxic, and capable of killing bacteria, viruses, and fungi. The second inventor, Marilyn L. Vail, suggested using eucalyptus oil and/or tea tree oil as potential candidates because of her prior research on these substances in her attempts to control *Candida albicans*.

The inventors identified a class of chemical compounds that may be used to prevent the invasion of pathogens into the respiratory system. They include eucalyptus oil and tea tree oil. The first inventor has found that routinely inhaling these substances has prevented him from getting any colds, flus, or pneumonia through the date of Sep. 6, 2002—a few days before the filing date of this application. The first inventor has been practicing the invention every day commencing on, or before, the first day of September of 1999. As a result of using the invention, the first inventor has had no respiratory infections for 3 years. This is despite the fact that the first inventor has had extensive business travels during this time. This is truly remarkable, because the first inventor has often been sick every several months or so before he began practicing the invention.

The first inventor performed experiments on himself with very crude apparatus. A small bottle of "eucalyptus rectified essential oil" made by "aroma-vera" was purchased. It had a blockage near the top of the bottle. Typically, the first inventor shook the bottle with the blockage "down" which caused eucalyptus oil to catch in the blockage near the top of the bottle. Then, with the bottle held with the blockage "up", and while holding one nostril closed, the first inventor would inhale very deeply through the other nostril thereby inhaling concentrated vapors of eucalyptus oil. Then the process was repeated with the other nostril. The first inventor estimates that the amount inhaled ranged between 0.001 milligrams to 100 milligrams, depending upon the circumstances, and the number of repetitions. The first inventor performed this inhalation immediately before he went "into public", such as into an enclosed public area having one or more human beings within that enclosed area. If there were sick people present that were coughing, or otherwise admitted that they had a cold, the flu, or pneumonia, the first inventor would thereafter similarly inhale concentrated vapors of eucalyptus oil every 30 minutes or so. By following this process, the first inventor has not had a cold, the flu, or pneumonia for the last 3 years.

The first inventor alternatively used tea tree oil in the above experiments and had similar results. The tea tree oil was in a small bottle marked with the legend "100% PURE AUSTRALIAN TEA TREE OIL" made by Desert Essence.

It is important to note that very strong vapors of either eucalyptus oil or tea tree oil were inhaled each time. This happened because of the close proximity of the nose to a pool of highly volatile fluids. However, there were several drawbacks to this method. As a first drawback, on occasion the fluids themselves got sucked up into the nose causing a very unpleasant situation. As a second drawback, if the fluids got on the hands, and then into the eyes, this was also an extraordinarily unpleasant, and perhaps, a dangerous situation. As a third drawback, inhalation through the mouth seemed relatively ineffective from vapors emanating from a simple bottle. As a fourth drawback, inhaling from a pool of highly volatile fluids on airplanes, in elevators, and in crowded resulted in others being subjected to the strong vapors of essential oils. Having open bottles of flammable fluids on an aircraft is not reasonable today. Accordingly, the inventors have designed an apparatus that provides very strong vapors that may be inhaled, but which also overcomes the above first, second and third drawbacks.

FIG. 1 shows a section view of an apparatus to conveniently generate vapors from eucalyptus oil that may be inhaled without suffering the above three drawbacks. Eucalyptus oil is chosen for this preferred embodiment, but the use of other suitable essential oils, such as tea tree oil, are discussed below. The apparatus in FIG. 1 is described as a hand-held "atomizer" that is generally designated with element 2. Eucalyptus oil 4 is shown in container 6. A piston 8 having O-ring 10 seals against the interior of the container wall. The atomizer has top element 12 that acts as a "button" (hereinafter "top button 12"), and the container has bottom 14. With one hand, placing the middle finger on the button 12 and the thumb on the bottom 14, and squeezing, produces the vaporized droplets of eucalyptus oil. One such droplet of eucalyptus oil is designated by numeral 16 that is shown in the location to be inhaled by the user.

The vapors of eucalyptus oil may be inhaled through the mouth, or through the nose, or through both. Holding one nostril closed at a time allows selective inhalation through one nostril, and then the other, so that the entire respiratory system may be entirely coated with the thin anti-pathogenic film of eucalyptus oil.

In FIG. 1, the atomizer is to be operated "substantially vertically" a term that will be defined below. Pressing down on button 12 increases the air pressure in air pocket 18 above the surface of the eucalyptus oil 20. This increasing pressure causes eucalyptus oil to flow through first entrance 21 of flexible tube 22 and then to first tube 24 that is in turn connected to the atomizer assembly 26. The first entrance 21 of the flexible tube is reinforced and constructed so that it does not collapse under use, and does not make a positive seal against the interior of the container walls that would interfere with functionality. Pressurized air flows thorough second entrance 28 of the second tube 30 that is in turn also connected to the atomizer assembly 26. Using typical designs for atomizers, and the like, the flow of eucalyptus oil and pressurized air into the atomizer assembly 26 generates particles of eucalyptus oil in the form of a vapor that pass through the exit passage 32 of the atomizer assembly. The atomizer assembly 26 may have any number of suitable valves, one-way valves, spring actuated valves, spring return valves, ball valves, spring loaded ball valves, breather orifices, etc., which are used in the art to make atomizers, and the like, for the purposes herein, however, those elements are not shown in FIG. 1 solely for the purposes of brevity. Any suitable "atomizer means" may be used for atomizer assembly 26.

In FIG. 1, the vaporized eucalyptus oil is injected from the exit passage 32 of the atomizer assembly into a cotton ball 34 whose edges are delineated with dashed lines in FIG. 1. Therefore, pushing down on button 12 causes vapors of eucalyptus oil to be injected into the cotton ball. Then, the vapors diffuse through the cotton ball for subsequent inhalation.

The tapered mouth orifice 36 is used to inhale vaporized eucalyptus oil by mouth. As vaporized eucalyptus oil and air is inhaled, any additional air required is provided through nostril orifice 38.

Alternatively, nostril orifice 38 is used to inhale vaporized eucalyptus oil by one nostril at a time. One nostril is held shut, and the other one is placed against nostril orifice 38 to inhale through a chosen nostril. One after another, both nostrils may be used to suitably inhale vapors of eucalyptus oil.

Other details are shown in FIG. 1. The upper body of the hand-held atomizer 40 is a one-piece unit having tapered mouth orifice 36 and nostril orifice 38. The upper body is attached to the piston 8 using typical fabrication techniques. The spacer 42 is designed to guide the main body 40 during its motion, and it serves as a retainer to prevent the piston 8 from inadvertently coming out of the container 6. The spacer 42 may also have one or more check-valves to function as "breathers" when the unit is initially filled with eucalyptus oil, respectively enumerated as 44 and 46, however these elements are not shown in FIG. 1 solely for the purpose of brevity. Spacer 42 has suitably close tolerances, or threads as necessary, to positively engage it to container 6.

FIG. 1 shows the position of piston 8 wherein the top portion of that piston is a distance designated by the legend "X" below the lower portion of the spacer 42. As the top button 12 is pushed downward, the piston 8 is also pushed downward thereby compressing spring 48, and the vaporized droplets of eucalyptus oil are formed. The "down stroke" causes the top of the piston to move through a maximum, and extreme value, of X. After completing the "down stroke", and upon removing finger pressure from the button, then compression spring 48 returns the top portion of the piston so as to make contact with the lower portion of the spacer 42, which is the "resting position" of the piston. Typical breather holes, one-way valves, such as ball valves, etc., are used to allow air to flow back into air pocket 18, thus preparing for the next "down stroke". Such a breather hole for the purposes herein is shown as element 50 that is located within a portion of atomizer assembly 26. In the "up stroke", and in this embodiment, air can flow into breather hole 50, and thereafter flow through second tube 30 to air pocket 18 thereby allowing the piston to return to its "resting position". Without such a breather hole, or the like, the piston might permanently stay in the "down stroke" position, or might stay in that position until other air leakages allowed the top of the piston to again contact the bottom portion of spacer 42. To achieve this functionality, various different preferred embodiments contemplate using any number of suitable valves, one-way valves, spring actuated valves, spring return valves, ball valves, spring loaded ball valves, breather orifices, etc., which are used in the art to make atomizers, and the like.

In FIG. 1, refilling the atomizer involves removing the spacer 42, removing the piston 8 from the container 6, and refilling the container. The piston 8 is then inserted into the container 6, and the spacer is reinstalled. Yet one or more ball valves in the piston (not shown) may be used to bleed off extra pressure in the event that is necessary during installation of the piston. Any such pressure relief valves shall have the numerals 52 and 54 respectively, but they are not shown in FIG. 1 solely for the purposes of brevity.

The hand-held atomizer overcomes several of the problems cited earlier. In relation to the above defined "first drawback", by using the cotton ball and the apparatus described, no fluids can get sucked up into a nostril. In relation to the above defined "second drawback", no liquids are generated exterior to the hand-held atomizer, so there is minimal chance of getting eucalyptus oil into the eyes. Further, the cotton ball also prevents liquids from being squirted directly into the eyes. In relation to the third drawback, the hand-held atomizer provides proper vaporized eucalyptus oil for inhalation by mouth. Therefore, the inventors have designed an apparatus and provided methods of operation that provide very strong vapors that may be inhaled, but which also overcome the previously defined first, second and third drawbacks.

There are many variations on the above preferred embodiment. The container 6 may be fabricated from any suitable material, including any type of plastic, or any type of transparent or translucent plastic of any coloration. Transparent or translucent plastics are convenient so that the presence or absence of the eucalyptus oil, and the surface of the eucalyptus oil 20, may be easily determined by visual inspection. The upper body of the hand-held atomizer 40 having tapered mouth orifice 36 and nostril orifice 38 may be made of any suitable material, including any type of plastic, or any type of transparent or translucent plastic of any coloration. Transparent or translucent plastics are convenient to determine the condition and extent of the cotton ball 34.

For proper operation, the cotton ball 34 should substantially fill and make contact with the interior walls of the upper body of the hand-held atomizer 40. The cotton ball 34 is convenient, but any material may be used as a substitute that has "cotton-ball like qualities" for the purposes of the invention herein that otherwise also avoids the above defined first, second, and third drawbacks. No toxic materials may be used to replace the cotton-ball. Spacer 42 may be fabricated from any material and may be disposed in its location in FIG. 1 using any suitable attachment methods including friction fitting, matching threads, retainer notches, and the like. Any suitable "retainer means" may replace spacer 42.

The dimensions of the nostril orifice 38 are chosen so that it conveniently extends beyond the radial extent of the container 6 and into the nostril for use when held in place by the fingers. The exterior of the container 6 has a first radius R1 (not shown in FIG. 1) that is typically ½ inches, and a first vertical length, or extent, L1 (not shown in FIG. 1) that is typically 1¾ inches tall. Here, the radius is defined as the radial distance away from the vertical axis of the container 6. For the record, FIG. 1 is not to scale. The nostril orifice 38 has a second radial extent R2 (not shown in FIG. 1) that is typically 1¼ inches and a nostril orifice diameter NOD (not shown in FIG. 1) that typically ranges between 3/16 inches O.D. to ¼ inches O.D. for convenient insertion into the nose, but many other dimensions are possible. The diameter NOD is chosen so that the nostril orifice can go into the interior of a typical nostril.

The tapered mouth orifice 36 has a third radial extent R3 (not shown in FIG. 1) that is typically 1½ inches, and an mouth inhalation diameter MID (not shown in FIG. 1) that is typically 1½ inches OD. The tapered mouth orifice may not be circular, and may be any suitably chosen shape to conveniently fit into the mouth. The overall maximum vertical dimension of the hand-held "atomizer", which is the distance between the button 12 and the bottom 14, is typically 3 inches.

In the above, it was stated that the atomizer is to be operated "substantially vertically". The atomizer is to be held in a "substantially vertical orientation" for proper operation. The definition of these terms are as follows. For proper operation, the first entrance 21 of the flexible tube must be immersed in the fluid 4, and must be located below the fluid level 20 so that fluid may be properly atomized ("first condition"). In the above embodiment, the second entrance 28 of the second tube is used to provide air under pressure to the atomizer assembly 26, so that the second entrance 28 must also be located above the fluid level 20 so for proper atomization of the fluid ("second condition"). Lastly, various means, including breather holes and suitable valves, have been described which allow the piston to return from the "down stroke" to its "resting position", and consequently, the orientation of the atomizer in FIG. 1 should be sufficiently vertical so as not to interfere with such means ("third condition"). Any hand-held "atomizer" that is generally designated with element 2 in FIG. 1 that is an orientation such that the first, second, and third conditions are satisfied in this paragraph is in a position that is "substantially vertical". Accordingly, the atomizer is operated "substantially vertically" which is in a "substantially vertical orientation". In general, when the atomizer is held in the hand, its longitudinal axis along its length is at an angle θ with respect to true vertical (which angle is not shown in FIG. 1 for brevity). This longitudinal axis is parallel to the vertical sides of the container 6. The maximum "tilt angle" at which the atomizer fails to meet the first, second, and third conditions depends upon the particular distance from the interior of the bottom of the container to the top of the fluid level 20, when the atomizer is held in the true vertical position, and that particular distance is identified by the legend Y in FIG. 1. Accordingly, there is reason to maintain a reasonable distance between the top of the fluid and the bottom of the piston, and that reasonable distanced is defined by the legend Z in FIG. 1. When X achieves its maximum value in the "down stroke" (XMAX) then Z maintains its minimum value at that position (ZMIN) for any given level of fluid in the container Y for θ=0 degrees. The variables XMAX, ZMIN and θ are not shown in FIG. 1 for the purposes of simplicity. The above comments may be suitably reformulated in terms of the volume of the fluid 4 inside the container 6. For future reference, the inside diameter of the container 6 is the parameter IDC, that is not shown in FIG. 1 for the purposes of brevity.

In earlier disclosure, element 16 was identified as a droplet of eucalyptus oil. There are two additional comments here. First, as is typical with most atomizer devices, there is a statistical distribution of droplet sizes and volumes produced depending upon a number of factors including the fluid, its viscosity, the design of the atomizer system, and the force applied to the button 12. The inventors include herein by reference all art in the field related to the production and measurements of such statistical distributions of droplet sizes. Second, any droplet 16 in FIG. 1 may also stand for any other droplet of any other fluid described to this point or hereafter in this application.

There are other variations of the apparatus. The functional elements in FIG. 1 may be reconfigured to fit onto a screw-on cap that in turn screws onto a bottle having eucalyptus oil. The bottle may in fact be the original bottle of eucalyptus oil that arrived from a manufacturer, so that the refilling process becomes easier. However, this is a minor variation of the invention, and in the interests of brevity, shall not be described in detail.

Tea tree oil may be substituted in the above for eucalyptus oil. Put another way, element 4 in FIG. 1 may be chosen to be tea tree oil instead. The use of tea tree oil in the apparatus is similar, except that it is possible that the atomizer assembly 26 may be changed because of the different properties that tea tree oil may have, including different viscosity, density, vapor pressure, etc. Each atomizer assembly may be specifically designed for the oil to be atomized. Each atomizer, or "atomizer means", may in fact be specific to different suppliers of tea tree oil or eucalyptus oil in that different suppliers may produce oils having different characteristics as they affect vaporization by the atomizer.

Yet further, element 4 may be chosen to be pure eucalyptus oil; pure tea tree oil; any mixture of eucalyptus oil and tea tree oil; any mixture of one or more components from eucalyptus oil and one or more components from tea tree oil (which components are defined below); any mixture of eucalyptus oil and distilled water; any mixture of tea tree oil and distilled water; and any mixture of eucalyptus oil, tea tree oil, and distilled water; and any mixture of the following—(a) one or more components from eucalyptus oil and (b) one or more components from tea tree oil and (c) any percentage of distilled water. Therefore, element 4 may be chosen to be any of the above defined fluids in FIG. 1.

Now, several additional topics are discussed below as they relate to the invention respectively entitled "Baseline Activities"; "Composition of Eucalyptus Oil"; "Comments About Eucalyptus Oil"; "Composition of Tea Tree Oil"; "Comments About Tea Tree Oil"; "Essential Oils"; "Eucalyptus Oil, Tea Tree Oil, and Prevention of Infections of Circulatory System and Prevention of Heart Attacks"; "Methods to Reduce Infections Following Operations"; 'The Phrase "To Prevent"'; and "References".

Baseline Activities

During the initial experiments lasting some six months commencing in September of 1999, the first inventor also did some other "baseline activities" that were important to maintain good lung health. To control his asthma, he inhaled twice a day Alupent® and Flovent® for the typical medical reasons. Further, the first inventor raised the head of his bed by about 4 inches to prevent gastric juices and related gasses from entering the respiratory system while sleeping. It may turn out that these "baseline activities" are important to the methods set forth in preferred embodiments of this invention. Usual experimental techniques will be used to determine their importance if necessary. As another statement of fact, the first inventor most often inhaled eucalyptus oil, but also often inhaled tea tree oil during this trial period. Another aspect of the invention includes the method of using eucalyptus oil and/or tea tree oil in combination with the use of Alupent® and Flovent® to prevent colds, flus, and pneumonia in individuals having asthma.

Prior to the inventor's routinely using the invention, the first inventor often inhaled Alupent® about 6 times a day and Flovent® about 6 times a day. If the first inventor stopped the use of these inhalers, he could hardly breath about 3 days later. During a series of experiments, the first inventor actually gave up the use of both of these asthma inhalers for a duration of 4 months. However, thereafter, the first inventor began to notice that his breathing was gradually becoming shallow. So, the first inventor began a regimen where he simply inhales Alupent® one time in the morning each day, and Flovent® one time in the morning every day. Those inhalers are left at home during the day, and the first inventor instead uses the invention herein. This regimen has worked for the first inventor for over 2 years. This approach has helped the first inventor to substantially avoid the well known side effects of asthma inhalers that are described in the book by Michael T. Murray, N.D., entitled "Natural Alternatives to Over-the-Counter and Prescription Drugs", William Morrow and Company, Inc., New York, N.Y., 1994, (Murray, 1994) an entire copy of which is incorporated herein by reference. In particular, please refer to Chapter 7 entitled "Asthma, Hay Fever, and Antihistamine Medications" in Murray, 1994.

Composition of Eucalyptus Oil

The chemical composition of eucalyptus oil is complicated and is known. There are various varieties, including oil from Eucalyptus australiana. See Hedges and Wilkens, 1991, an entire copy of which is incorporated herein by reference describes oil from that species. Page 345 of this reference states in part:

"Analysis of Eucalyptus oil, like that of any complex mixture, presents difficult problems not only in the separation but also in identification of components. Terpenes and terpene derivatives constitute the bulk of the oil (1, 2) and, due to the inherent flexibility of the isoprene units which comprise the compounds, the oil contains many closely related isomers and homologs. Further characterization reveals that 40–80% of the oil is composed of one compound, 1,8-cineole, thus presenting the choromatographer with a large sample dynamic range problem."

Hedges and Wilkens, 1991, on page 345, further state: "A *Eucalyptus australiana* oil sample was obtained . . . ".

Hedges and Wilkens, 1991, on page 346, further state: "Fifty-eight peaks were counted in the chromatogram of *E. Australiana.*"

Hedges and Wilkens, 1991, on page 347, in "Table 1. Component identification by CG-1R-MS" list the following compounds as being present, or likely present, in Eucalyptus oil: $\alpha$-pinene; 1,8-cineole; limonene; $\alpha$-terpinene; 2,3-dimethylcyclohexanol; cis-linalool oxide; terpinolene; $\rho$-cymenene; $\alpha$-pinene oxide; linalool; isopentyl isovalerate; fenchyl alcohol; $\alpha$-campholenal; 3,3,6,6-tetramethyltricyclo [3.1.0.02.4]hexane; trans-verbenol; 2,5-dimethyl benzaldehyde; borneol; 4-terpineol; 1-methyl phenyl ethanone; $\alpha$-terpineol; $\alpha$-hexyl cinnamaldehyde; 4-isopropenyl-1-methy cyclohexenel; para-mentha-1(7), 8,10-dien-9-ol; $\rho$-carvone; 1-methylethyl-2-methylene cyclohexanone; geraniol; isoborneol acetate; $\alpha$-terpinenyl acetate; $\beta$-patchoulene; geranyl $\eta$-propionate; $\beta$-gurjunene; aromadendrene; and allo-aromadendrene. Different preferred embodiments of this invention contemplate using one or more of the above components in any proportion to achieve the desired results. Further, all routine techniques used in the medical and biological sciences are incorporated herein by reference, and these standard techniques may be used to identify one or more of the above compounds as being the active ingredients to obtain the desired results. Once so identified, the individual compound or mixture of compounds are merely different preferred embodiments of the invention disclosed herein.

Further information concerning the detailed chemical analysis of eucalyptus oil are provided in references 1–25 on page 350, of Hedges and Wilkens, 1991, and entire copies of all such 25 references are incorporated herein by reference.

An earlier reference, Gunther, 1948, provided an older list of ingredients of eucalyptus oil. An entire copy of Gunther, 1948, is incorporated herein by reference. In particular, see pages 437–525, of Volume IV of this reference. For different varieties of eucalyptus oils, and sources for those oils, please also see Schnaubelt, 1998; Lawless, 1999; and Rose, 1999; entire copies of which are incorporated herein by reference.

Comments about Eucalyptus Oil

Balch and Balch, 1997, page 69, state under "Action and Uses" for eucalyptus oil the following: "Clears congestion, has a mild antiseptic action, and reduces swelling by helping to increase blood flow. Relaxes tired and sore muscles. Good for colds, coughs, and other respiratory disorders." This reference on page 69, also states under "Comments" concerning eucalyptus oil: "Recommended for external use only. It should not be used on broken skin or open cuts or wounds."

Miller and Miller, 1995, state on page 251, the following: "Eucalyptus is one of the most commonly used essential oils. You could write a book on all its uses. There are over 700 varieties of eucalyptus, some growing to 500 feet, and they all possess similar properties. It is currently used in many allopathic medical preparations. It is one of the three best oils for use with any respiratory tract problems because the component eucalyptol is mucolytic (it relaxes the flow of mucous) and it excretes the eucalyptol out though the lung surface. Even if you take it internally in tea form, eucalyptus will very quickly pass out of the body through the lungs, having its relaxing effect to the mucous membranes. As it is inhaled it gives an immediate effect; then again as it circulates out of the body." This reference further recites certain additional formulas "including rosemary and camphor". This reference further states with regards to "Actions": "diaphoretic, decongestant, stimulant, antiseptic, antispasmodic, alternative, diuretic, expectorant, antipyretic, regenerative, lowers blood sugar, disinfects the air, increases concentration, deodorant, germicidal".

Fugh-Berman, 1997, on page 194, states the following warnings about potential toxicity: "Essential oils should only be taken orally under the supervision of a practitioner experienced in their use. Tea Tree oil and eucalyptus oil have been associated with childhood poisonings, [Jacobs, Webb] and ingestion of pennyroyal oil has killed at least two adults. [Sullivan, Vallance] Essential oils are safe to use topically if diluted (and a few are safe full-strength)." These references are listed below under "References" so that the interested reader can further investigate the toxicity of eucalyptus oil and other essential oils.

Only AFTER the inventors had conceived the inventions herein, and only AFTER the personal trials conducted by the first inventor had been completed, the inventors found a hard-to-locate newsletter entitled "Alternatives For the Health Conscious Individual", written by Dr. David G. Williams. In particular in the October, 1999 issue of Williams, 1999, on page 25, Dr. Williams states in part: "The essential oil extracted from the leaves has long been used in cough drops and cold medications, mouthwashes, toothpaste, detergents, and liniments for arthritis pain." This reference further states on page 25: "In fact, millions of people take advantage of eucalyptus' antimicrobial properties each day by swishing with that old medicine chest staple, Listerine." That reference on page 25, also states: "Thanks in large part to the eucalyptus, Listerine is a very potent germ-killer . . . " This article further states that Listerine® "can kill 60 percent of the HIV virus it touches within 30 seconds. In this same time period, Listerine killed 100 percent of the bacteria *Staphylococcus aureus* present."

Williams, 1999, page 26, then recounts several anecdotal stories. In one, and during a trip to Australia when "the winter flu season was in full swing", he noticed that almost everyone he "encountered had succumbed to this flu with the notable exception of two cleaning ladies" each of which "carried a small rag that had been doused with the oil of eucalyptus". In their presence, the "fumes were very strong . . . ".

Williams, 1999, page 26, then recounts a discussion with the above cleaning ladies: "When I questioned the ladies, they told me that one of their grandfathers had used eucalyptus oil to ward of flu since World War I. At that time, a military base had apparently experienced a flu epidemic so sever the soldiers were dying from it. To stop the problem, authorities sealed off one of the barracks and sprayed down the interior with eucalyptus oil. Then they placed all the solders in that building for a day. That action reportedly stopped the epidemic in 24 hours."

Williams, 1999, page 26, further states: "Eucalyptus oil can be toxic if taken internally, but breathing the oil's fumes will likely allow its bactericidal components to knock out infections in the nasal passages, sinuses, bronchial tubes, and lungs." Williams, 1999, page 26, then suggests by analogy to carrying around rags soaked with eucalyptus oil that it "can actually prevent the flu", but he gives no mechanism for doing so, and provides no methods of doing so—except carrying around rags soaked with eucalyptus oil or soaking a room like the barracks with the oil. Williams, 1999, page 26, further states: "I'am currently investigating a very unusual eucalyptus variety that is non-toxic when taken orally. If it checks out, this development will open up all kinds of fantastic medicinal possibilities." Apparently, Dr. Williams is primarily concerned with orally taken medication.

Therefore, Williams, 1999, states or implies that eucalyptus oil may be effective against certain viruses and against certain bacteria. However, the methods set forth in Williams, 1999, of providing such vapors to human beings are not practical in their normal lives. Normal human beings cannot carry around rags soaked with eucalyptus oil that would produce odors offensive to others. Nor is it practical to lock people up in a barracks or other rooms washed down with eucalyptus oil. Several preferred embodiments of this invention are provided to overcome these problems.

Williams, 1999, does NOT describe the methods or apparatus disclosed in the preferred embodiments herein. Williams, 1999, does not describe directly inhaling the fumes periodically from an inhalant device as a method to prevent infection. Williams, 1999, does not describe any type of thin anti-pathogenic layer or barrier that substantially prevents the initial infection of colds flus, and other pathogens for a period of time following the inhalation of eucalyptus oil. Williams, 1999, does not describe the proposed use of eucalyptus oil as a prophylactic agent to prevent the initial infection of tuberculosis. Williams, 1999, does not describe methods of infection proposed by the inventor involving a "likely pathogenic invasion site", and the use of inhaled vapors of eucalyptus oil to decrease the risk of invasions or infections of such sites by pathogens. Nor does Williams, 1999, describe the possibility that infectious diseases may involve the progression of colonies of pathogens vs. time that may involve viral, bacterial, and fungal elements defined earlier as "symbiotic pathogens", and that the initial infection of these pathogens may be prevented by the periodic inhalation of strong vapors from eucalyptus oil.

Further, Williams, 1999, does not describe any method to reduce the risks of infection of the human respiratory system by pathogens that includes at least the step of the inhalation of concentrated vapors from eucalyptus oil immediately before entering an enclosed public area having one or more human beings within said enclosed area.

Still further, Williams, 1999, does not describe the method to prevent the initial infection of the human respiratory system by pathogens causing diseases such as colds, flus and pneumonia, that includes at least the step of inhaling concentrated vapors of eucalyptus oil to form an anti-pathogenic barrier inside the human respiratory system that is effective for a period of time of at least 30 minutes following said inhalation. Nor does Williams, 1999, describe periodic inhalations of vapors from eucalyptus oil to maintain the anti-pathogenic barrier inside the human respiratory system.

Another reference, Igram, 1992, page 18, states the following:

"Eucalyptus oil is used for the purpose of healing the respiratory passages, and the amount that actually entered the tissues is minimal."

Schnaubelt, 1998, describes in on pages 31–40, and elsewhere, the antibacterial, antiviral, and antifungal effects of certain essential oils. For example, Schnaubelt, 1998, page 33, refers to another study which showed that various essential oils had varying effectiveness against different pathogens including "Pneumococcus spec., *Klebsiella pneumoniae, Staphylococcus aureus haemolyticus, Neisseria catarrahalis, Streptococcus haemolyticus, Proteus vulgaris, Haemophilus influenzae, Haemophilus* pertusis" and "*Candida albicans*, and *Escherichia coli*-Aerobacter group, various Cornybacteria, *Listeria*".

Composition of Tea Tree Oil

The chemical composition of tea tree oil is complicated and is known. See Swords and Hunter, 1978, an entire copy of which is incorporated herein by reference. Page 734 of this reference states in part:

"Australian tea tree oil (*Melaleuca alternifolia*) was fractionated by column chromatography and analyzed by combined gas chromatograhy-mass spectrometry. Preparative GLC of selected fractions yielded pure compounds for analysis by infrared and nuclear magnetic resonance spectroscopy. Forty compounds were identified, including viridiflorene which has not previously reported as occurring in nature." Swords and Hunter, 1978, on page 734–735, further state:

"The chemical composition of tea tree oil has been previously investigated by the Instrumental Laboratories of Fritzsche Brothers, Inc.; New York, and the following components were reported (Gunther, 1968): α-pinene, 2.2%; α-terpinene, 7.5%; limonene, 1.0%; 1,8-cineole, 5.6%; γ-terpinene, 17.5%; ρ-cymene, 3.0%; terpinolene, 3.1%; 1-terpinen-4-ol, 44.9%, α-terpineol, 5.2%; aromadendrene, 21.7%; two unknown sesquiterpenes, 1.6% each."

Swords and Hunter, 1978, on page 737, show "Table I" which presents the list of compounds present, or suspected to be present, in tea tree oil as follows: 1. α-Pinene; 2. Camphene; 3. β-Pinene; 4. Sabinene; 5. Myrcene; 6. α-Phellandrene; 7. 1,4-Cineole; 8. α-Terpinene; 9. Limonene; 10. 1,8-Cineole; 11. γ-Terpinene; 12. p-Cymene; 13. Terpinolene; 14. Hexanol; 15. Allyl hexanoate; 16. ρ, α-Dimethylstyrene; 17. a Sesquiterpene; 18. α-Cubebene; 19. a Sesquiterpene; 20. α-Copaene; 21. Camphor; 22. α-Gurjunene; 23. Linalool; 24. a Sesquiterpene; 25. Unidentified; 26. 1-Terpineol; 27. 1-Terpinen-4-ol; 28. β-Elemene; 29. Caryophyllene; 30. a Sesquiterpene; 31. Aromadendrene; 32. β-Terpineol; 33. Alloaromadendrene; 34. Unidentified; 35. Humulene; 36. Unidentified; 37. γ-Muurolene; 38. α-Terpineol; 39. Viridiflorene; 40. Piperitone; 41. α-Muurolene; 42. Piperitol; 43. Unidentified; 44. σ-Cadinene; 45. 4,10-Dimethyl-7-isopropyl bicyclo [4.4.0]-1,4-decadiene; 46. Nerol; 47. 8-ρ-Cymenol; and 48. Calamenene. Capital letters were used here for various compounds because they were so listed in Table 1 in Swords and Hunter, 1978.

Lawless, 1994, pages 22–23, states the following:

"The Australian standard for Melaleuca alternifolia oil now requires that the terpinen-4-ol content of the oil should be greater than 30 percent, and the cineole content less than 15 percent. A top quality tea tree oil should, however, have a maximum cineole content of 5 percent and a minimum terpinen-4-ol content of 35–40 percent. As the demand for tea tree has increased, the essential oil has also been increasingly subjected to adulteration, usually with cineole—the main constituent of eucalyptus oil which gives eucalyptus oil its characteristic camphor-like scent." This reference further goes on to state: "The balance of the main constituents in a fresh, high quality tea tree oil should be approximately as follows: Alpha-pinene 2.5 percent; Alpha-terpinene 9.1 percent; Para-cymene 3.9 percent; 1,8-cineole 4.3 percent; Gamma-terpinene 24.6 percent; Alpha-terpineol 2.3 percent; Terpinen-4-ol 42.1 percent; (and) Terpinolene 4.1 percent."

In the above quotation from Lawless, 1994, pages 22–23, the ';' and the word 'and' were added to the previous quote to make it readable solely for the purposes of brevity in accordance with rules of the USPTO for specification.

A more recent reference was obtained from the internet concerning the constituents of tea tree oil. This was obtained from the company called "Hans-Dieter Knoch Tea Tree Export" on Mar. 9, 2000 at the world-wide web address of "www.midcoast.com" that lists the following ingredients as a "Typical Analysis" from Batch No. HK008: alpha-pinene 1.3%; sabinene 1.3%; alpha-terpinene 9.4%; Limonene 1.1%; p-cymene 2.5%; 1,8 cineole 2.9%; gamma-terpinene 20.2%; terpineolene 3.4%; Terpinen-4-ol 38.2%; alpha-terpineol; 2.4%; Aromadendrene 2.4%; Ledene 1.4%; delta-cadinene 1.6%; Glubolul 0.5%; and Viridiflorol 0.4%.

Comments about Tea Tree Oil

It is of interest to note that item 21 in Table I of Swords and Hunter, 1978, (discussed above) is "Camphor", that is specified as one ingredient in Mentholatum® Ointment. However, the statement on a container of this ointment in the possession of the inventors reads as follows: "Gentle aromatics help relieve stuffy noses, chest congestion, sinus congestion, head colds, chest colds, and muscular aches due to coughs and colds." The label on the container does NOT make any statement about prevention of colds or flus by using the product.

Fugh-Berman, 1997, page 193, states the following: "Tea tree oil is widely used as an antibacterial and antifungal topical medication, and several studies indicate its effectiveness. One compared pure tea tree oil and the antifungal drug clotrimazole for treatment of fungal infection of the toenails. After six months, the two treatments were found to be equally effective."

Lawless, 1994, on pages 25–26, states the following:

"Due to its unique composition, tea tree oil displays a number of remarkable properties making it very effective for a wide range of complaints. Foremost among these properties, and what makes tea tree oil outstanding in comparison to other remedies, is that it is active against all varieties of infections organisms: bacteria, fungi and viruses. Independent microbiological testing has confirmed the effectiveness of tea tree oil against a wide range of micro-organisms, notably:

Gram Positive bacteria: *Staphyloccus aureus, Staphyloccus epidermidis, Staphyloccus pneumoniae, Staphyloccus faecalis; Staphyloccus pyrogenes, Staphyloccus agalactiae*, Propionibacterium acnes, Beta haemolytic streptococcus Gram Negative bacteria: *Escherichia coli, Klebsiella pneumonia, Citrobacter* spp., *Shigella sonnei, Proteus mirabilis, Legionella* spp., *Pseudomonas aeruginosa*

Fungi: *Trichophyton mentagrophytes, Trichophyton rubrum, Aspergillus niger, Aspergillus flavus, Candida albicans, Microspourm canis, Microsporum gypseum, Thermoactinomycetes vulgarism.*

Lawless, 1994, page 26, further states:

"Tea tree's effectiveness in fighting infection is further backed up by its ability to stimulate the immune system—this means that if the body is threatened by any of these organisms, tea tree increases the body's own ability to protect itself and to respond appropriately. Tea tree oil's main areas of activity may therefore be summarized as: antiseptic/bactericidal, anti-fungal, anti-viral, and immuno-stimulant."

Regarding the antiviral properties of tea tree oil, Lawless, 1994, page 27, states:

"Viruses are the invading organisms responsible for most epidemic illnesses. As a powerful anti-viral agent, tea tree is effective in fighting many common infectious diseases such as measles, chickenpox, flu, colds and shingles as well as other viral complaints such as cold sores, veruccae and warts."

Regarding the immuno-stimulant properties of tea tree oil, Lawless, 1994, pages 27–28, further states:

"In this context, tea tree is principally of great value as a preventative remedy—to help the body fight off all kinds of infection. This is especially important if the body is already in a weakened condition brought on by either stress, illness or the use of anti-biotics or other drugs which have lowered the body's natural resistance levels. Tea tree has been found to be especially helpful for those who need to have their strength built up, such as before a surgical operation or for those suffering from chronic or long-standing debilitating illnesses such as glandular fever or hepatitis. Its possible application to AIDS is also currently being researched."

Lawless, 1994, on pages 18–24, describes the chemical make-up of tea tree oil. On page 20, it states in part: "In its natural state, tea tree oil is an extremely complex chemical substance containing at least 48 organic compounds. The main constituents are terpenes, pinenes, cymones, terpineols, cineole, sesquiterpines and sesquiterpinene alcohols—however, it also contains four constitutions that are rarely found elsewhere in nature: viridiflorene (approximately 1 percent), B terpineol (0.24 percent), L-terpineol (trace) and allyhexanoate (trace).[1]" The reference cited at the end of this quote is Swords and Hunter, 1978, although the recitation is misspelled in Lawless, 1994 on page 112.

Following a percentage break-down of substances within tea tree oil, Lawless, 1994, on page 23, further states:

"It is interesting to note that none of the these substances is especially effective alone. It is only in combination that these substances demonstrate their maximum healing power—which is known as a 'synergy'. This is a quality common to many essential oils, where the unique balance of constituents, including the trace elements, contributes to the overall effectiveness of the remedy. This factor also helps to account for why synthetically produced products, or 'nature-identical' oils, cannot match properties exhibited by the naturally derived original, since it is very difficult to mimic the complex and diverse blend of components found in nature."

Igram, 1992, on page 17, states in part: "It should be emphasized that tea tree oil is an antiseptic." Igram, 1992, further states: "This is not to suggest that tea tree oil is exceptionally toxic when taken internally. There are no deaths on record from internal use or accidental overdose."

Igram, 1992, further states on page 17:

"Tea tree oil finds its greatest usage as a remedial agent for diseases affecting the exposed surfaces and mucous membranes. It can be safely used in small doses on all mucous membranes, including the gums, oral mucosa, vagina, urethra, colon and rectum. Although internal ingestion has been attempted without noticeable toxic effects, this is not enough evidence to warrant its widespread use internally."

With regards to the respiratory system, Igram, 1992, page 18, states with regard to tea tree oil: "It can be inhaled to help relive bronchial congestion and to aid in opening clogged sinus passages."

Further, tea tree oil penetrates tissues deeply. Regarding this subject, Igram, 192, page 54, states the following:

"One of the major obstacles in eradicating *Candida* infections, as well as other fungal infections, is getting the medicine to penetrate deep enough into the site of the invention. If a person weeds a garden by mowing the weeds only, they will grow right back. The cure is achieved by digging the weeds out by the roots, or in today's age, destroying the roots with chemicals. In a similar manner it is crucial to utilize medicines which penetrate as deeply as possible into the skin and mucous membranes. This is precisely the advantage of tea tree oil. It has the greatest penetrating capacity of any known antifungal agent. As it saturates the tissues, it kills fungal organisms on contact."

However, Olsen, 1991, points out that under apparently comparatively rare circumstances, that there are adverse affects related to the use of tea tree oil. For example, on page 14, of Olsen, 1991, it states the following: "Tea Tree Oil was tested recently in 1991 in a family practice office. Fifty patients with various skin problems were chosen at random." The reference continues with: "One patient dropped out of the study and a second discontinued due to a mild erythematous skin sensitivity to the 100% oil. This was the only side-effect reported." The reference further states: "The results of using the Tea Tree Oil were striking. All the patients but one were cured or showed remarkable improvement of the conditions treated."

Olsen, 1997, page 11, states the following:

"ISO Standard 4730 states that tea tree oil should be extracted from *Melaleuca alternifolia, Melaleuca linafolia*, or *Melaleuca dissitifolia* species of the Myrtaceae family. Other tea tree species, including Cajuput (*Melaleuca Cajuputi*), New Zealand Manuka (*Leptospermum scoparium*), New Zealand Ti-Tree (*Cordyline australis*), and Kanuka (*Leptospermum ericoides*) are not highly regarded, as they do not contain the same anti-microbial benefits, nor have they been in use for nearly a century as has *Melaleuca alternifolia*."

Further, Olsen, 1997, on page 12, presents typical "Analytical Results" that presents the chemical composition and percentages present for a sample from the Australian Plantations, Jul. 17, 1997, which is incorporated herein by reference.

Yet further, Olsen, 1997, on page 83, states the following:

"Action. Pure tea tree oil conforming to Australian standard A.S.D. 175, revised 1985 (AS 2782-1985) and 1996 (ISO 4730) is a powerful broad-range antiseptic, fungicide, and bactericide. The main component is terpinen-4-ol (T-4-ol). Optimal activity at 35–40% w/v. Its bacterial actions is increased in the presence of blood, serum, pus, and necrotic tissue. It is able to penetrate deeply into infected tissue and pus, mix with these, and cause them to slough off while leaving a healthy surface. The oil has a very low toxicity, and is virtually a non-irritant event to sensitive tissues. Because of its lower cineole level, tea tree oil is less toxic and less irritating that eucalyptus oil. Be aware that some unknown eucalyptus oils have been blended with a synthetic form of terpinen-4-ol, which alters the chemical composition."

Essential Oils

The "essential oils" are defined on page 63, of Balch and Balch, 1997, as follows:

"Essential oils are derived from herbs or other plants through steam distillation or cold pressing. They are usually mixed with a vegetable oil or water, and used either as a mouth, ear, or eye wash, or as an inhalant, douche, or tea. These oils can also be used externally in massage or on burns and abrasions. Essential oils readily combine with the natural fats present in the skin. With few exceptions, such as the use of camphor, eucalyptus, or tea tree oil for certain skin conditions, essential oils should always be diluted in either water or oil before being applied to the body, and they should not be taken internally except under the direction of a physician trained in their use."

Prime examples of essential oils are eucalyptus oil and tea tree oil. In one preferred embodiment of the invention, vapors are alternatively inhaled, first from eucalyptus oil, and then from tea tree oil, to prevent colds, flu, and the like. This is the so-called "alter method" of using essential oils. The rationale for using such an approach is to avoid a build-up of immunity developed by organisms to just one substance. Further, eucalyptus oil may preferentially affect one set of pathogens, and tea tree oil may affect another set of pathogens, in a complex disease that may have bacterial, viral, and fungal elements.

Different embodiments of the invention contemplate using any essential oil known that has at least the following properties: it is non-toxic when inhaled; and it has anti-pathogenic properties. Many such essential oils are listed in Gunther, 1948; in Schnaubelt, 1998; in Lawless, 1999; in Olsen, 1997; and in Rose, 1999.

In addition to mixtures of essential oils that may substitute for element 4 in FIG. 1 that have already been listed above, element 4 in addition may be chosen to be any one of the following: any mixture of eucalyptus oil with tea tree oil; any mixture of eucalyptus oil with one or more other essential oils; any mixture of tea tree oil with one or more other essential oils; any mixture of eucalyptus oil, tea tree oil, with one or more other essential oils; any mixture of eucalyptus oil, tea tree oil, one or more essential oils, and distilled water; any mixture of (a) one or more components from eucalyptus oil, (b) one or more components from tea tree oil and (c) one or more components from any other essential oil; and any mixture of (a) one or more components from eucalyptus oil, (b) one or more components from tea tree oil, (c) one or more components from any other essential oil, and (d) any portion of distilled water. Typical procedures in the art may be used to determine the optimum percentage mixtures of any of the above components to prevent colds, flus, and infections of the human respiratory system. Therefore, element 4 in FIG. 1 may include any of the above listed fluids.

For the purposes herein, the term "essential oils" include all ingredients from the plant *Lomatium dissectum*. This plant was referred to in Schnaubelt, 1998, on page 39, with the following quote:

"As shown by Indians of the Pacific Northwest, placing more faith in a much broader effectiveness of essential oils against viral illnesses is more justified than the paucity of scientific studies would suggest. These Indians were able to protect themselves against the devastating consequences of the worldwide flu epidemic of 1918 with a preparation made from a native plant, *Lomatium dissectum*[8]." Here, the superscript refers to Alstat, 1987.

The following is a list of "essential oils". The scientific name is on the left-hand side, and the common name appears in parentheses.

*Abies alba* (Fir, Silver)
*Abies balsamica* (Fir, Balsam)
*Abies grandis* (Fir, Grand)
*Abies siberica* (Fir, Siberian)
*Achillea millefolium* (Yarrow, Blue)
*Amni Visnaga* (Amni Visnaga)
*Angelica archangel* (Angelica Seed)
*Angelica archangel* (Angelica Root)
*Aniba roseodora* (Rosewood)
*Anthemis nobilis* (Camomile, Roman)
*Apium graveolens* (Celery)
*Artemisia dracunculus* (Tarragon)
*Artemisia Herba Alba* (Mugwort, White, Thujone)
*Betula alleganiensis* (Birch, Yellow)
*Boswellia frerana* (Frankincense)
*Cananga odorata* (Ylang Ylang)
*Canarium luzonmicum* (Elemi)
*Carum carvi* (Caraway)
*Cedrus deodara* (Cedar, Himalayan)
*Cedrus atlantica* (Cedar, Atlas)
*Cinnamonum camphora* (Camphor)
*Cinnamonum zeylanicum* (Cinnamon Bark)
*Cistus landi.* var. *pinene* (Cistus [Rockrose])
*Citrus aurantifolia* (Petitgrain, Lime)
*Citrus aurantifolia* (Lime)
*Citrus aurantium* (Orange, Sweet)
*Citrus aurantium amara* (Neroli)
*Citrus aur. bergamia* (Bergamot)
*Citrus aur. bigarade* (Orange, Bitter)
*Citrus aur. bigarade* (Petitgrain, Bigarade)
*Citrus limonum* (Lemon, Yellow)
*Citrus paradisi* (Grapefruit)
*Citrus paradisii* (Grapefruit Pink)
*Citrus reticulata* (Petitgrain, Mandarine)
*Citrus reticulata* (Tangerine)
*Citrus reticulata* (Mandarine, Red)
*Citrus sinensis* var. (Orange, Red)
*Coriandrum sativum* (Coriander)
*Cupressus* (Cypress)
*Cymbopogon citratus* (Lemongrass)
*Cymbopogon flexuosus* (Lemongrass)
*Cymbopogon martini* (Palmarosa)
*Cymobogon nardus* (Citronella)
*Daucus carota* (Carrot Seed)
*Eletteria cardamomum* (*Cardamon*)
*Eucalyptus citriadora* (Eucalyptus citriadora)
*Eucalyptus globulus* (Eucalyptus, Sweet)
*Eucalyptus radiata* (Eucalyptus radiata)
*Eucalyptus smithii* (Eucalyptus smithii)
*Eugenia caryophyllata* (Clove Bud)
*Ferula Galbaniflua* (Galbanum)
*Foeniculum dulce* (Fennel, Sweet)
*Gaulteria fragrantissima* (Wintergreen)
*Helichr.* ital. var. *serot.* (*Helichrysum* Serotinum)
*Hypericum perforat.* (St. John's Wort)
*Hyssopus* off. var. *dec.* (Hyssop, Decumbens)
*Hyssopus officinalis* (Hyssop)
*Inula graveolens* (Inula, Extra Fine)
*Iris Pallida* (Iris [Orris])
*Jas. offic. sambac* (Jasmine Sambac)
*Jasminum grandiflor.* (Jasmine, Grandiflorum)
*Juniperus communis* (Juniper, Berry)
*Juniperus com.* var. *alp.* (Juniper, Alpine)
*Juniperus virginiana* (Cedar, Va.)
*Laurus nobilis* (Bay Laurel)
*Lavandula angustifolia* (Lavender)
*Lavandula hybrida* (Lavandin, Sweet)
*Lavandula latifolia* (Lavender, Spike)
*Lavendula officinalis*
*Lavandula officinalis* var. *veraE* (Lavandin, Sweet)
*Lavandula officinalis* var. *vera* (Lavender, Extra)
*Lippia citriodora* (Lemon Verbena)
*Litsea cubeba* (*Litsea cubeba*)
*Majorana hortensis* (Marjoram, Sweet)
*Matricaria chamom.* (Camomile, Ger.)
*Melaleuca alternifolia* (Tea-Tree)
*Melaleuca quinquinervera* (Niaouli)
*Melissa officinalis* (Melissa [Lemon Balm])
*Mentha piperita* (Peppermint)
*Mentha silvestris* (Mint, Forest)
*Mentha spicata* (Spearmint)
*Myristica fragrans* (Nutmeg)
*Myrtus communis* (Myrtle, Green)
*Myrtus communis* (Myrtle, Red)
*Nardostachys jatamansi* (Spikenard [Nardo])
*Ocimum basilicum* (Basil, Holy)
*Ocimum basilicum* (Basil, Tropical)
*Ocimum basilicum* (Basil, Sweet, Linalol)
*Ocotea cymbar* (Sassafras)
*Origanum compactum* (Oregano)
*Origanum vulgare* (Oregano)
*Pelargonium graveolens* (Geranium)
*Pelargonium roseum* (Geranium, Rose)
*Petroselinum crispum* (Parsley Seed)
*Pimenta racemosa* (Bay Leaf)
*Pimpinella anisum* (Anise)
*Pinus nigra* (Pine, Black)
*Pinus nigra, pinaster* and *sylvestris* (Pine des Alpes)
*Pinus sylvestris* (Pine Sylvestre)
*Piper nigrum* (Pepper, Black)
*Pistacia lentiscus* (Mastic)
*Pogostemon cablin* (Patchouli)
*Poliantes tuberosa* (Tuberose)
*Pseudotsuga menzesieii* (Fir Douglas)
*Ravensara aromatica* (Ravensare)
*Rosa damascena* (Rose Otto)
*Rosa damascena* (Rose
*Rosmarinus officinalis* (Rosemary)
*Salvia lavandulifolia* (Sage, Spanish)
*Salvia officinalis* (Sage)
*Salvia sclarea* (Clary Sage)
*Santalum album* (Sandalwood, Tamil Nadu)
*Satureia montana* (Savory)
(?) (Sea Pine)
*Styrax benzoe* (Benzoin resinoid 50%)
*Syzygium aromaticum* (Clove)
*Tagetes patula* (Tagetes)
*Tanacetum annuum* (Camomile, Blue)
*Tsuga canadensis* (Spruce, Hemlock)
*Thymus mastichina* (Marjoram, Spanish)
*Thymus satureioides* (Thyme Borneol)
*Thymus serpyllium* (?)

*Thymus vulgaris* (Thyme Linalol)
*Thymus vulgaris* (Thyme Thujanol)
*Thymus zygis* (Thyme, Red, Thymol)
*Vanilla Planifolia* (Vanilla)
*Vetiveria zizanoides* (Vetiver)
*Zingiber officinale* (Ginger, $CO_2$)

Various embodiments of the invention contemplate using the vapors from any one of the above essential oils. Other embodiments contemplate using the vapors from a mixture in any relative proportion of two of the above listed essential oils. Yet other embodiments contemplate using the vapors from a mixture in any relatively proportion of two or more of the above essential oils.

Eucalyptus Oil, Tea Tree Oil, and Prevention of Infections of Circulatory System and Prevention of Heart Attacks Several studies have been performed involving the expectorant effects of various essential oils. See Schnaubelt, 1998, pages 39–40, that describes results from several other references. A relevant point for this analysis is that a "clinical study determined the terpine levels in blood of test subjects after they inhaled essential oils." That reference further states: "Within thirty to forty minutes the concentration of essential oils absorbed through inhalation sinks to half its original value. This demonstrates that there is no danger of accumulating essential oils in the body even with repeated uses."

Further, Schnaubelt, 1998, on pages 98–99, shows that the inhalation of essential oils results in essential oils being provided to the "heart-lung-circulatory system". Recent literature points to irritations, or inflammations, of the circulatory system caused by unknown pathogens as being associated with certain forms of heart disease. For example, according to page A7, of The Seattle Times, Friday, Mar. 24, 2000, researchers identified "levels of C-reactive protein (CRP)" as an indicator for heart attacks. This article states "The protein indicates if arteries are inflamed."

To my knowledge, the quoted researchers do not know what pathogens cause the inflammation in the circulatory system. However, since eucalyptus oil and tea tree oil have antibacterial, antiviral, and antifungal properties, no matter what the type of pathogen is involved, then the periodic inhaling of concentrated vapors from eucalyptus oil and/or tea tree oil may be used as an effective preventative measure against the development of this type of heart disease and the resulting heart attacks.

Therefore, inhaled vapors from eucalyptus oil and tea tree oil enter the blood stream and are useful to reduce the inflammation caused by pathogens to reduce the probability of heart attacks.

Further, a preferred embodiment of the invention is a method to reduce inflammation of the human circulatory system caused by pathogens to prevent heart attacks that includes at least the step of inhaling concentrated vapors of eucalyptus oil so that said oil enters the circulatory system, whereby said tea tree oil possesses antibacterial, antiviral, and antifungal properties useful to reduce any the inflammation.

Another preferred embodiment is the method to reduce inflammation of the human circulatory system caused by pathogens to prevent heart attacks that includes at least the step of inhaling concentrated vapors of tea tree oil so that said oil enters the circulatory system, whereby said tea tree oil possesses antibacterial, antiviral, and antifungal properties useful to reduce any the inflammation.

Similar comments apply to other essential oils that are non-toxic when inhaled, that possess antibacterial, antiviral, and antifungal properties useful to reduce any inflammation within the circulatory system.

Methods to Reduce Infections Following Operations

A major cause of deaths in hospitals in the United States are attributed to infections following operations. For example, see the book entitled "To Err is Human, Building a Safer Health System", "Advanced Copy", published by the Institute of Medicine, National Academy of Sciences, that is listed under Kohn, et al., 1999 in the "References" below. Perhaps a dear cousin in my family fell victim recently to such an infection. A device similar to the atomizer shown in FIG. 1 could be used to reduce the probability of infection following many operations. In this case, nostril orifice 38 could be blocked off, or it could instead attached to a sterile source of flowing gas, such as air or nitrogen.

This preferred embodiment provides the method to generate and cause a mist of droplets of tea tree oil and distilled water to flow to the open wound in the human body during major surgery. The tea tree oil and distilled water mist would form an antibacterial, antiviral, and antifungal barrier against infection from the dreadful types of infections pathogens present in typical operating rooms. Other embodiments contemplate using various different mixtures of tea tree oil, other essential oils, and distilled water.

The Phrase "To Prevent"

The above disclosure has described methods to prevent the initial infection of the human respiratory system by pathogens causing diseases such as colds, flus and pneumonia, that includes at least the step of inhaling concentrated vapors of eucalyptus oil to form an anti-pathogenic barrier inside said respiratory system that is effective for a period of time of at least 30 minutes following said inhalation.

The above disclosure has also described methods to prevent the initial infection of the human respiratory system by pathogens causing diseases such as colds, flus and pneumonia, that includes at least the step of inhaling concentrated vapors of tea tree oil to form an anti-pathogenic barrier inside said respiratory system that is effective for a period of time of at least 30 minutes following said inhalation.

The above paragraphs have used the word "prevent". In typical drug tests regulated by the FDA (the Food and Drug Administration), Phase I, Phase II, Phase III, and sometimes, Phase IV trials are carried out. See page 16, of Fugh-Berman, 1997. The word "prevent" is often used herein in a statistical manner. As pointed out on pages 11–13, of Fugh-Berman, 1997, a drug must provide benefit that is "statistically significant" over the so-called "placebo effect", where subjects report improvements in up to ⅓ of the cases. In several of the preferred embodiments, the word "prevent" means to provide "statistically significant" benefits against infection over the so-called "placebo effect".

Because of the statistical nature of the word "prevent", several of the above embodiments describe methods to reduce the risks of infection of the human respiratory system by pathogens that includes at least the step of the inhalation of concentrated vapors from eucalyptus oil immediately before entering an enclosed public area having one or more human beings within said enclosed area.

In the previous paragraph, pathogens include viruses, bacteria, fungi, tuberculosis, and infectious agents causing pneumonia.

One way to conduct trials on the above methods to prevent diseases are "randomized trials". See Fugh-Berman, 1997, page 12. For example, during the next flu season, perhaps 10 children's day care centers could be chosen. Then, on a random basis, ½ of the teachers in the children's day care centers could periodically inhale eucalyptus oil and/or tea tree oil to prevent colds and flus. Then, the results could be compared to the ½ of the teachers that did not do so. Then, the same group could be swapped. Standard statistical analysis can then be used to determine the statistical effectiveness of the preventative methods.

In several embodiments above, it is stated that eucalyptus oil and/or tea tree oil provide a barrier against infection by pathogens. These barriers include a direct barrier, but also include other "barrier-like effects". The inhaled oils soak into the cells within the respiratory system that provides additional protection against infection by pathogens. The oils reduce any pre-existing infection caused by pathogens, and therefore, in conjunction with the immune system, again provides additional protection against infection by pathogens. The oils help mucous membranes repair themselves, and so this effect also provides additional protection against infection by pathogens. The oils help repair many types of existing damage and therefore, this effect also provides additional protection against infection by pathogens.

Tuberculosis

An important reference on Tuberculosis is made in the book by Mark H. Beers, M.D. and Robert Berkow M. D, Editors, that appears as a the Publication on the World Wide Web (http://www.merck.com/pubs/mmanual/) entitled "The Merck Manual of Diagnosis and Therapy", "Seventeenth Edition", "Centennial Edition", Merck & Co., Whitehouse Station, N.J., 1999 (Beers, et al., 1999), an entire copy of which is incorporated herein by reference. In particular, Section 13 (Infectious Diseases), Chapter 157 (Bacterial Diseases) under the topic of "Caused by Mycobacteria" and "Tuberculosis" of Beers, et al., 1999, is particularly relevant, and entire copy of which is incorporated herein by reference.

Section 13 (Infectious Diseases), Chapter 157 (Bacterial Diseases) and under the topic of "Caused by *Mycobacteria*" and "Tuberculosis" of Beers, et al., 1999, states the following.

Under the topic of Etiology, Epidemiology, and Incidence, it states the following:

"TB refers only to disease caused by *Mycobacterium tuberculosis, Mycobacterium bovis* or *Mycobacterium africanum*. Other mycobacteria cause disease similar to TB (see below), but they generally respond poorly to drugs that are effective for TB."

"In developed countries, human TB occurs almost exclusively from inhalation of organisms dispersed as droplet nuclei from a person with pulmonary TB whose sputum smear is positive. *M. Tuberculosis* may float in the air for several hours, thus increasing the chance of spread. Spread can occur in mycobacteriology laboratories and autopsy rooms, in part because the hydrophobic nature of the organism facilitates aerosolization. Fomites appear to play no role in their spread."

"Signs of a potentially very dangerous epidemic of TB have already appeared. The advent of HIV infection has created the circumstances not only for an increased incidence of TB (up 30% in New York State in 1992 to 1993) but also for the development of organisms resistant to all first-line drugs. The incidence of TB increased from 1989 to 1992, but since then more strict control measures appear to have been effective.

However, the threat of drug-resistance organisms remains."

Under the subtitle of "Pulmonary Tuberculosis" related to the above paragraph, it states the following:

"Typically, recrudescent disease occurs in nodular scars in the apex of one or both lungs (Simon foci) and may spread through the bronchi to other portions."

Under the topic of "Other *Mycobacteria* Infections Resembling Tuberculosis" it states the following:

"*Mycobacteria* other than the tubercle *bacillus* can cause infections in humans. These organisms are commonly found in the environment (soil and water), and exposure is more frequency than development of disease. Since all of the organisms are less virulent than M. Tuberculosis, a defect in local or systemic host defense is usually a precondition for disease. *M. avium* complex (MAC)—the closely related species of *M. avium* and *M. intracellulare*—accounts for most of the diseases. Other noteworthy species are *M. kansasii, M. xenopi, M. marinum, M. ulcerans*, and *M. fortuitum* complex (*M. fortuitum* and *M. chelonei*).

Under the subtopic of "Pulmonary Disease" related to the above paragraph, it states:

"Most pulmonary infections involve MAC, but a few are due to *M. kansassi, M. xenopi*, and *M. fortuitim* complex. The typical patient is a middle-aged white man with prior lung problems such as chronic bronchitis, emphysema, healed TB, bronchiectasis, or silicosis."

Please refer to the article by Eugene Sherry, M.D. and P. H. H. Warnke, Ph.D, entitled "Alternative for MRSA and Tuberculosis (TB): Eucalyptus and Tea-Tree Oils as New Topical Antibacterials", Poster Board Number: P376, 2002 Annual Meeting of the American Academy of Orthopaedic Surgeons, Dallas, Tex., Feb. 13–17, 2002, (Sherry and Warnke, 2002), an entire copy of which is incorporated herein by reference.

Sherry and Warnke, 2002, confirm that Eucalyptus Oil and Tea Tree Oils are useful to combat TB methicillin-resistant staphylococcal) (MRSA) infections. Applicant has already disclosed the use of eucalyptus oil and tea tree oil in relation to tuberculosis in U.S. patent application Ser. No. 09/542,703 that was filed on Apr. 3, 2000. For example, in Ser. No. 09/542,703, please see lines 29–33 on page 1; lines 28–31 on page 3; and lines 14–16 of page 44. application Ser. No. 09/542,703 discusses *staphylococcus aureus* on lines 3–4, page 25; page 28, line 12; and line 10, page 32. The invention disclosed in Ser. No. 09/542,703 discloses Eucalyptus Oil and Tea Tree Oils as being effective against a variety of pathogens, including those listed in this paragraph.

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many of the pathogens that cause tuberculosis which are listed above within this section.

Therefore, the following general statements may be made.

In accordance with the invention, the inhalation of the vapor from 50% *Eucalyptus globulus* and 50% *Melaleuca alternifolia* can be used to prevent tuberculosis.

In accordance with the invention, the inhalation of the vapor from 50% *Eucalyptus globulus* and 50% *Melaleuca alternifolia* can be used to prevent the initial infection of bacteria that cause tuberculosis.

In accordance with the invention, the inhalation of the vapor from 50% *Eucalyptus globulus* and 50% *Melaleuca alternifolia* can be used to cure tuberculosis.

In accordance with the invention, the inhalation of the vapor from 50% *Eucalyptus globulus* and 50% *Melaleuca alternifolia* can be used to cure the infections of bacteria that cause tuberculosis.

In accordance with the invention, the inhalation of the vapor from 50% *Eucalyptus globulus* and 50% *Melaleuca alternifolia* can be used to treat tuberculosis.

In accordance with the invention, the inhalation of the vapor from 50% *Eucalyptus globulus* and 50% *Melaleuca alternifolia* can be used to treat the infections of bacteria that cause tuberculosis.

In accordance with the invention, the inhalation of the vapor from any mixture of *Eucalyptus globulus* and *Melaleuca alternifolia* can be used to prevent tuberculosis.

In accordance with the invention, the inhalation of the vapor any mixture of *Eucalyptus globulus* and *Melaleuca alternifolia* can be used to prevent the initial infection of bacteria that causes tuberculosis.

In accordance with the invention, the inhalation of the vapor from any mixture of *Eucalyptus globulus* and *Melaleuca alternifolia* can be used to cure tuberculosis.

In accordance with the invention, the inhalation of the vapor from any mixture of *Eucalyptus globulus* and *Melaleuca alternifolia* can be used to cure the infection of bacteria that cause tuberculosis.

In accordance with the invention, the inhalation of the vapor from any mixture of *Eucalyptus globulus* and *Melaleuca alternifolia* can be used to treat tuberculosis.

In accordance with the invention, the inhalation of the vapor from any mixture of *Eucalyptus globulus* and *Melaleuca alternifolia* can be used to treat the infection of bacteria that cause tuberculosis.

The No Sinus Pain™ Inhaler manufactured by Inhalation, Inc. is a preferred embodiment of the invention used to prevent, treat or cure tuberculosis.

In accordance with the invention, the antipathogenic properties of vapors from any essential oil listed on the above defined List of Essential Oils can be tested in the apparatus defined in the "Test Chamber" dated Oct. 11, 2001 that is a part of Provisional Patent Application No. 60/328, 912. Those vapors showing antipathogenic properties against the pathogens causing tuberculosis can be identified using that apparatus and the procedures described in the Provisional Patent Application. That essential oil may then be provided in one or more of the Inhaler apparatus shown in Provisional Patent Application No. 60/328,912. Inhaled vapors from that Inhaler apparatus may be used to prevent or cure tuberculosis.

In accordance with the invention, the antipathogenic properties of vapors from any mixture of essential oil listed on the above defined List of Essential Oils can be tested in the apparatus defined in the "Test Chamber" dated Oct. 11, 2001 that is a part of Provisional Patent Application No. 60/328,912. Those vapors showing antipathogenic properties against the pathogens causing tuberculosis can be identified using that apparatus and the procedures described in the Provisional Patent Application. That essential oil may then be provided in the Inhaler apparatus shown in Provisional Patent Application No. 60/328,912. Inhaled vapors from that Inhaler Apparatus may be used to prevent or cure tuberculosis.

Specific mixtures of essential oils of interest to be tested in the above "Test Chamber" apparatus are listed as follows:

Mixture #1

One or more of the following mixed together:
A. *Eucalyptus globulus;*
B. *Melaleuca alternifolia;*
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia montana*; and
G. different varieties of Thyme including *Thymus satureioides, Thymus serpyllium, Thymus vulgaris*, and *Thymus zygis.*

For Example: Mixture #1A

A. 50% *Eucalyptus globuls;*
B. 25% *Melaleuca alternifolia;*
C. 5% by volume of *Uegenia caryophyllata;*
D. 5% by volume of *Cinnamonun camphora;*
E. 5% by volume of *Oreganum vulagare;*
F. 5% by volume of *Satureia Montana*; and
G. 5% by volume of *Thymus vulgaris.*

Mixture #2

One or more of the following mixed together:
A. *Eucalyptus globulus* (at least 30% by volume);
B. *Melaleuca alternifolia* (at least 30% by volume)

With at least one of the following oils added:
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia Montana*; and
G. different varieties of Thyme including *Thymus satureioides, Thymus serpyllium, Thymus vulgaris*, and *Thymus zygis.*

For Example: Mixture #2A

A. *Eucalyptus globulus* (at least 30% by volume);
B. *Melaleuca alternifolia* (at least 30% by volume)
C. *Origanum vulgare* (less than 40%)

Mixture #3

One or more of the following mixed together:
A. different varieties of Eucalyptus oil *Eucalyptus citriadora, Eucalyptus globulus, Eucalyptus radiata*, and *Eucalyptus smithii*
B. *Melaleuca alternifolia;*
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia Montana;*

G. different varieties of Thyme including *Thymus satureioides, Thymus serpyllium, Thymus vulgaris*, and *Thymus zygis;*

For Example: Mixture #3A

A. 25% by volume of *Eucalyptus globulus;*
B. 25% by volume of *Eucalyptus citriodora;*
C. 25% by volume of *Melaleuca alternifolia;*
D. 5% by volume of *Uegenia caryophyllata;*
E. 5% by volume of *Cinnamonun camphora;*
F. 5% by volume of *Oreganum vulagare;*
G. 5% by volume of *Satureia Montana;* and
H. 5% by volume of *Thymus vulgaris.*

Mixture #4

One or more of the following mixed together:
A. different varieties of Eucalyptus oil *Eucalyptus citriadora, Eucalyptus globulus, Eucalyptus radiata*, and *Eucalyptus smithii* (at least 30% by volume)
B. *Melaleuca alternifolia* (at least 30% by volume);

With at least one of the following oils added:
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia montana;*
G. different varieties of Thyme including *Thymus satureioides, Thymus serpyllium, Thymus vulgaris*, and *Thymus zygis;*

For Example: Mixture #4A

A. *Eucalyptus globulus* (at least 20% by volume)
B. *Eucalyptus citriodora* (at least 20% by volume)
C. *Melaleuca alternifolia* (at least 40% by volume)
D. *Origanum vulgare* (less than 20% by volume)

Mixture #5

One or more of the following mixed together:
A. different varieties of Eucalyptus oil *Eucalyptus citriadora, Eucalyptus globulus, Eucalyptus radiata*, and *Eucalyptus smithii*
B. *Melaleuca alternifolia;*
C. different varieties of Clove oil including *Eugenia caryophyllata* and *Syzygium aromaticum;*
D. different varieties of Cinnamon including *Cinnamonum camphora* and *Cinnamonum zeylanicum;*
E. different varieties of Oregano including *Origanum vulgare;*
F. different varieties of Savory including *Satureia Montana;*
G. different varieties of Thyme including *Thymus satureioides, Thymus serpyllium, Thymus vulgaris*, and *Thymus zygis;*
H. different varieties of Cajeput including *Melaleuca cajeputi;*
I. different varieties of Geranium including *Pelargonium roseum* and *Pelargonium graveolens.*
J. different varieties of Lavender including *Lavandula hybrida, Lavandula latifolia, Lavandula officinalis* var., and *Lavandula officinalis* var. *vera;*
K. different varieties of Myrtle including *Myrtus communis;*
L. different varieties of *Niaouli* including *Melaleucea quinquinervera*
M. different varieties of Petitgrain including *Citrus aurantifolia, Citrus* aur. *bigarade* and *Citrus arantium amara.*
N. different varieties of Pine oil including *Pinus nigra, Pinus nigra, pinaster* and *sylvestris, Pinus sylvestris*, and Sea Pine; and
O. different varieties of Tarragon including *Artemisia dracunculus;*

For Example: Mixture #5A

A. 25% by volume of *Eucalyptus globulus;*
B. 10% by volume of *Eucalyptus citriodora;*
C. 10% by volume of *Eucalyptus radiata;*
D. 25% by volume of *Melaleuca alternifolia;*
E. 2% by volume of *Uegenia caryophyllata;*
F. 2% by volume of *Cinnamonun camphora;*
G. 2% by volume of *Oreganum vulagare;*
H. 2% by volume of *Satureia Montana;*
I. 2% by volume of *Thymus vulgaris;*
J. 10% *Melaleuca cajeputi;* and
K. 10% *Lavendula officinalis.*

In the above mixtures, "eucalyptus oil" is *Eucalyptus globulus*, and "tea tree oil" is *Melaleuca alternifolia.*

The vapors from Mixture #1, Mixture #2, Mixture #3, Mixture #4 and Mixtures #5 above may be used to prevent, treat, and cure tuberculosis.

Opportunistic Infections by Pathogens in Lungs of Patients Having with Cystic Fibrosis Please refer to book by Balch, J. F., and Balch, P. A., that is entitled "Prescription for Nutritional Healing", Third Edition, Avery Publishing Group, Garden City Park, New York, N.Y., 2000 ("Balch and Balch, 2000"), an entire copy of which is incorporated herein by reference.

Page 311 of Balch and Balch, 2000, states in part under the topic of "Cystic Fibrosis":

"Cystic fibrosis (CF) is the most common inherited illness among Americans of northern and western European ancestry. It occurs in people of all ethnic backgrounds and is most common in Caucasians. It occurs with approximately equal frequency in men and women."

"One in every 3,000 children in the United States is born with the disorder. It is estimated that 8 million Americans are silent carriers of the defective gene that leads to this disease. The gene responsible for CF was identified in 1989 on human chromosome 7, and it encodes instructions for a protein that regulates the passage of salt in and out of the cells of the body's endocrine glands. This defective gene transforms the protein (called the cystic fibrosis transmembrane conductance regulator [CFTR]) and causes it to produce a mucus too thick and too abundant for the body to excrete."

"The airway, gastrointestinal tract, bile ducts of the liver, ducts of the pancreas, and the male genitourinary tract all produce mucus. Cystic fibrosis alters this normally protective mucus and transforms it into a thick, abnormal excretion that obstructs airways and damages tissue. Symptoms of CF begin early in life. Glands in the lungs and bronchial tubes secrete large quantities of thick, sticky mucus that blocks lung passages and provides the perfect place for harmful bacterial to thrive. *Pseudomonas aeruginosa* (also common in cancer and burn patents) is the bacteria that most commonly colonizes the lungs, resulting in chronic coughing and wheezing, difficulty breathing, and recurrent lung infections. Once established, the bacteria remain in the lungs and are responsible for repeated outbreaks of infection. They form their own dense structure, called a biofilm, and are immune to most current treatments. They also produce toxic proteins that can cause tissue damage and weaken the immune system. The lungs of many children with CF are inhabited or colonized by the *Pseudomonas aeruginosa* bacteria before they are ten years of age."

An importance reference in this field appears under the topic of "General" under Section 19 (Pediatrics), Chapter 267 (Cystic Fibrosis) Beers, et al., 1999, an entire copy of which is incorporated herein by reference.

Section 19 (Pediatrics), Chapter 267 (Cystic Fibrosis) in Beers, et al., 1999, states in part:

"Evidence suggests that the lungs are histologically normal at birth. Pulmonary damage is probably initiated by diffuse obstruction in the small airways by abnormally thick mucus secretions. Bronchiolitis and mucopurulent plugging of he airways occur secondary to obstruction and infection. Bronchial changes are more common than parenchymal changes. Emphysema is not prominent. As the pulmonary process progresses, bronchial walls thicken; the airways fill with purulent, viscid secretions; areas of atelectasis develop; and hilar lymph nodes enlarge. Chronic hypoxemia results in muscular hypertrophy of the pulmonary arteries, pulmonary hypertension, and right ventricular hypertrophy. Much of the pulmonary damage may be caused by immune-mediated inflammation secondary to the release of proteases by neutrophils in the airways. Bronchoalveolar lavage fluid, even early in life, contains large number os neutrophils and increased concentrations of free neutrophil elastase, DNA, and interleukin-8."

"Early in the course, *Staphylococcus aureus* is the pathogen most often isolated from the respiratory tract, but as the disease progresses, *Pseudomonas aeruginosa* is most frequently isolated. A mucoid variant of *Pseudomonas* is uniquely associated with CF. Colonization with *Burkholderia* capacia occurs in up to 7% of adult patients and may be associated with rapid pulmonary deterioration."

Vapors from the 50% *Eucalyptus globulus* and 50% *Melaleuca alternifolia* mixture of essential oils are broadly antipathogenc. Those vapors are effective against many of the pathogens on the above defined list. In particular, they are effective against many of the pathogens that invade the lungs of patients with cystic fibrosis that are listed above within this section.

Therefore, the following general statements may be made.

In accordance with the invention, the inhalation of the vapor from 50% *Eucalyptus globulus* and 50% *Melaleuca alternifolia* can be used to prevent infection of the lungs of patients having cystic fibrosis by pathogens that include *Pseudomonas aeruginosa*.

In accordance with the invention, the inhalation of the vapor from 50% *Eucalyptus globulus* and 50% *Melaleuca alternifolia* can be used to prevent the initial infection by bacteria that infect the lungs of patients having cystic fibrosis.

In accordance with the invention, the inhalation of the vapor from 50% *Eucalyptus globulus* and 50% *Melaleuca alternifolia* can be used to cure infections of *Pseudomonas aeruginosa* in the lungs of patients having cystic fibrosis.

In accordance with the invention, the inhalation of the vapor from 50% *Eucalyptus globulus* and 50% *Melaleuca alternifolia* can be used to cure infections of bacteria that infect the lungs of patients having cystic fibrosis.

In accordance with the invention, the inhalation of the vapor from 50% *Eucalyptus globulus* and 50% *Melaleuca alternifolia* can be used to treat infections of the lungs of patients having cystic fibrosis by pathogens that include *Pseudomonas aeruginosa*.

In accordance with the invention, the inhalation of the vapor from 50% *Eucalyptus globulus* and 50% *Melaleuca alternifolia* can be used to treat the infections of bacteria that infect the lungs of patients having cystic fibrosis.

In accordance with the invention, the inhalation of the vapor from any mixture of *Eucalyptus globulus* and *Melaleuca alternifolia* can be used to prevent infection of the lungs of patients having cystic fibrosis by pathogens that include *Pseudomonas aeruginosa*.

In accordance with the invention, the inhalation of the vapor any mixture of *Eucalyptus globulus* and *Melaleuca alternifolia* can be used to prevent the infection by bacteria that infect the lungs of patients having cystic fibrosis.

In accordance with the invention, the inhalation of the vapor from any mixture of *Eucalyptus globulus* and *Melaleuca alternifolia* can be used to cure infections of *Pseudomonas aeruginosa* in the lungs of patients having cystic fibrosis.

In accordance with the invention, the inhalation of the vapor from any mixture of *Eucalyptus globulus* and *Melaleuca alternifolia* can be used to cure infections of bacteria that infect the lungs of patients having cystic fibrosis.

In accordance with the invention, the inhalation of the vapor from any mixture of *Eucalyptus globulus* and *Melaleuca alternifolia* can be used to treat infections of the lungs of patients having cystic fibrosis by pathogens that include *Pseudomonas aeruginosa*.

In accordance with the invention, the inhalation of the vapor from any mixture of *Eucalyptus globulus* and *Melaleuca alternifolia* can be used to treat infections of bacteria that infect the lungs of patients having cystic fibrosis.

Similar statements to the above 12 statements are hereby made by reference with regards to the specific pathogen *Staphylococcus aureus* and to the specific pathogen *Burkholderia cepacia*.

The No Sinus Pain™ Inhaler manufactured by Inhalation, Inc. is a preferred embodiment of the invention used to prevent, treat, or cure opportunistic infections of the human respiratory system of those individuals having cystic fibrosis.

A pertinent reference is the book entitled "Aromatherapy for Health Professionals, by Shirely Price and Len Price, Second Edition, Churchill Livingstone, New York, N.Y., 1999 (Price and Price, 1999), an entire copy of which is incorporated herein by reference. In particular, page 70 has Table 4.4 that shows that "*Melaleuca alternifolia* [TEA TREE]" is particularly effective against the pathogen *Pseudomonas aeruginosa*. An entire copy of Table 4.4 is also incorporated herein by reference.

In accordance with the invention, the antipathogenic properties of vapors from any essential oil listed on the above defined List of Essential Oils can be tested in the apparatus defined in the "Test Chamber" dated Oct. 11, 2001 that is a part of Provisional Patent Application No. 60/328,912. Those vapors showing antipathogenic properties against the pathogens causing infections within the lungs of patients having cystic fibrosis can be identified using that apparatus and the procedures described in the Provisional Patent Application. That essential oil may then be provided in one or more of the Inhaler apparatus shown in Provisional Patent Application No. 60/328,912. Inhaled vapors from that Inhaler apparatus may be used to prevent, treat, or cure infections of the lungs by bacteria that include *Staphylococcus aureus, Pseudomonas aeruginosa*, including a mucoid variant of that bacteria, and *Burkholderia capacia*.

In accordance with the invention, the antipathogenic properties of vapors from any mixture of essential oil listed on the above defined List of Essential Oils can be tested in the apparatus defined in the "Test Chamber" dated Oct. 11, 2001 that is a part of Provisional Patent Application No. 60/328,912. Those vapors showing antipathogenic properties against the pathogens infecting the lungs of patients having cystic fibrosis can be identified using that apparatus and the procedures described in the Provisional Patent Application. That essential oil may then be provided in the Inhaler apparatus shown in Provisional Patent Application No. 60/328,912. Inhaled vapors from that Inhaler Apparatus may be used to prevent, treat, or cure infections of the lungs by bacteria that include *Staphylococcus aureus, Pseudomonas aeruginosa*, including a mucoid variant of that bacteria, and *Burkholderia capacia*.

The vapors from Mixture #1, Mixture #2, Mixture #3, Mixture #4 and Mixtures #5 above may be used to prevent, treat, and cure opportunistic infections associated with cystic fibrosis.

Clearing Partially Obstructed Sinuses

The inventors performed many experiments with various mixtures of eucalyptus oil and tea tree oil. These mixtures were used in various inhalers. It was found that the mixture of 50% eucalyptus oil and 50% tea tree oil produced vapors that when inhaled, opened partially obstructed sinuses within 30 seconds to 2 minutes. This effect has been verified repeatedly.

Other mixtures of eucalyptus oil and tea tree oil have similar properties. Therefore, another embodiment of the invention is the method of inhaling the vapors from any mixture of eucalyptus oil and tea tree oil to open partially clogged sinuses. In this case, the eucalyptus oil was *Eucalyptus globulus*, and the tea tree oil is *Melaleuca alternifolia*.

Many individuals report that the No Sinus Pain™ Inhaler manufactured by the firm Inhalation, Inc. may be used to open up partially clogged sinuses within 30 second to 2 minutes. Here the phrase "partially obstructed sinuses" may be used interchangeable with the phrase "partially clogged sinuses".

Curing Cluster Headaches

During various experiments with essential oils, the inventors investigated using the vapors from mixtures of essential oils to cure cluster headaches. For some individuals, they describe a cluster headache as very painful, and often describe the pain like that coming from "an ice pick behind an eyeball". In the cases of 4 adult females to date, the inhaled vapors from a mixture of *Lavandula hybrida* ("Lavandin"), *Metha piperita* ("Peppermint") and *Betula alleghaniensis* ("Birch") have relieved the symptoms of cluster headaches within minutes after inhalation. One adult female also inhales the vapors to prevent the onset of routine cluster headaches near ovulation or menstruation.

Therefore, another embodiment of the invention is the method of inhaling any mixture containing Lavandin, Peppermint, and Birch to prevent, treat or cure cluster headaches. Yet another embodiment of the invention is the method of inhaling any mixture containing Lavandin, Peppermint, and Birch to prevent, treat or cure any type of headache.

Several individuals claim that the inhalation of vapors from the No Head Ache" Inhaler manufactured by Inhalation, Inc. have cured their cluster headaches.

Relaxation

The inventors have also performed many experiments with mixtures of *Lavandula angustifolia* ("Lavender oil") and *Eucalyptus globulus* ("Eucalyptus oil"). Inhaling the very concentrated vapors from Lavender oil have proved to be unpleasant. Consequently, adding Eucalyptus oil to the Lavender Oil makes it more pleasant to inhale. In this process, the inventors have discovered that the inhaled vapors from any mixture of Lavender oil and Eucalyptus oil produces a sense of calm and relaxation. This effect is more pronounced if the amount of Lavender oil exceeds 50% of the mixture.

Inhalation, Inc. manufactures the No Stress, No Nerves" Inhaler having a mixture of Lavender oil and Eucalyptus oil, where the fraction of Lavender oil exceeds 50% of the mixture. Several individuals have stated that inhaling the vapors from the No Stress, No Nerves™ Inhaler produces a calming effect.

A pertinent reference to this subject is the book entitled "Aromatherapy for Health Professionals, by Shirely Price and Len Price, Second Edition, Churchill Livingstone, New York, N.Y., 1999 (Price and Price, 1999), an entire copy of which is incorporated herein by reference. In particular, the following statement is made of page 75: "*Lavandula angustifolia* is well known for its sedative effect but rather less known for its ability to prevent sleep at high doses (observed and experienced by many aromatherapists)."

Inhalation, Inc.

The inventors have formed Inhalation, Inc. to commercialize their inventions. As of this date, this firm manufactures and provides the following inhalers:

No Colds, No Flus™ Inhaler that contains 100% *Eucalyptus globulus* ("Eucalyptus oil").

No Sinus Pain™ Inhaler that contains a mixture of *Eucalyptus globulus* ("Eucalyptus oil") and *Melaleuca alternifolia* ("Tea Tree oil").

The No Head Ache™ Inhaler that contains a mixture of *Lavandula hybrida* ("Lavandin"), *Metha piperita* ("Peppermint") and *Betula alleghaniensis* ("Birch").

The No Stress, No Nerves™ Inhaler that contains a mixture of *Lavandula angustifolia* ("Lavender oil") and *Eucalyptus globulus* ("Eucalyptus oil")

The No Asthma Attack" Inhaler that contains 100% *Eucalyptus globulus* ("Eucalyptus oil").

Several physicians are now using these inhalers in their normal practices.

Summary

In accordance with the above, any combination of Eucalyptus oil and Tea Tree oil may be used for various preferred embodiments of the invention.

Accordingly, it is evident that a preferred embodiment of the invention is a method to reduce the risks of infection of the human respiratory system by *Staphylococcus aureus* in an enclosed public area having one or more human beings within the enclosed area comprising the following steps:
- (a) within a period of time of 30 minutes before entering the public area, inhaling from a hand-held atomizer apparatus the concentrated vapors from a mixture of a first percentage of eucalyptus oil with the remaining component comprised of tea tree oil; and
- (b) after entering the public area, periodically inhaling from the hand-held atomizer apparatus the concentrated vapors from the mixture, whereby the period of time between successive inhalations exceeds 30 minutes, and whereby the period of time between successive inhalations is less than 2 hours; and whereby the first percentage of eucalyptus oil is selected from a list comprising 1% eucalyptus oil, 5% eucalyptus oil, 10% eucalyptus oil, 20% eucalyptus oil, 30% eucalyptus oil, 40% eucalyptus oil, 50% eucalyptus oil, 60% eucalyptus oil, 70% eucalyptus oil, 80% eucalyptus oil, 90% eucalyptus oil, 95% eucalyptus oil, and 99% eucalyptus oil; and whereby the concentrated vapors are generated within the hand-held atomizer apparatus; and whereby the concentrated vapors are inhaled through at least one orifice attached to the hand-held atomizer apparatus.

In accordance with the above, another preferred embodiment of the invention is a method to reduce the risks of infection of the human respiratory system by *Pseudomonas aeruginosa* in an enclosed public area having one or more human beings within the enclosed area comprising the following steps:
- (a) within a period of time of 30 minutes before entering the public area, inhaling the concentrated vapors from a mixture of 50% of eucalyptus oil and 50% tea tree oil, whereby the concentrated vapors are generated within a hand-held atomizer apparatus, and whereby the concentrated vapors are inhaled through at least one orifice attached to the hand-held atomizer apparatus; and
- (b) after entering the public area, periodically inhaling the concentrated vapors from the mixture in the hand-held atomizer apparatus, whereby the period of time between successive inhalations exceeds 30 minutes, and whereby the period of time between successive inhalations is less than 2 hours;

and whereby infections from *Pseudomonas aeruginosa* are known to cause fatal lung infections of individuals having cystic fibrosis.

In accordance with the above, yet another preferred embodiment of the invention is a method to reduce the risks of infection of the human respiratory system by *Burkholderia capacia* in an enclosed public area having one or more human beings within the enclosed area comprising the following steps:
- (a) within a period of time of 30 minutes before entering the public area, inhaling the concentrated vapors from a mixture of 50% of eucalyptus oil and 50% tea tree oil, whereby the concentrated vapors are generated within a hand-held atomizer apparatus, and whereby the concentrated vapors are inhaled through at least one orifice attached to the hand-held atomizer apparatus; and
- (b) after entering the public area, periodically inhaling the concentrated vapors from the mixture in the hand-held atomizer apparatus, whereby the period of time between successive inhalations exceeds 30 minutes, and whereby the period of time between successive inhalations is less than 2 hours;

and whereby infections from *Burkholderia capacia* are known to cause fatal lung infections of individuals having cystic fibrosis.

In accordance with the above, yet another preferred embodiment of the invention is a method to reduce the risks of infection of the human respiratory system by *Mycobacterium tuberculosis* in an enclosed public area having one or more human beings within the enclosed area comprising the following steps:
- (a) within a period of time of 30 minutes before entering the public area, inhaling the concentrated vapors from a mixture of 50% of eucalyptus oil and 50% tea tree oil, whereby the concentrated vapors are generated within a hand-held atomizer apparatus, and whereby the concentrated vapors are inhaled through at least one orifice attached to the hand-held atomizer apparatus; and
- (b) after entering the public area, periodically inhaling the concentrated vapors from the mixture in the hand-held atomizer apparatus, whereby the period of time between successive inhalations exceeds 30 minutes, and whereby the period of time between successive inhalations is less than 2 hours;

and whereby infections from *Mycobacterium tuberculosis* are known to cause serious infections of the human respiratory system.

REFERENCES

The above recited references are defined as follows, entire copies of which are incorporated herein by reference:

Alstat, E., in the paper entitled "Lomatium Dissectum, An Herbal Virucide", in the journal called "Complementary Medicine", May/June 1987, pages 32–33 ("Alstat, 1987") [Ed Alstat]

Anderson, K. N., Anderson, L. E., and Glanze, W. D., Editors, the book entitled "Mosby's Medical Dictionary", Fourth Edition, Mosby-Year Book Inc., St. Louis, Mo., 1994 ("Anderson, et al., 1994")

Audesirk, T., and Audesirk, G., the book entitled "Biology, Life on Earth", Fourth Edition, Prentice Hall, Upper Saddle River, N.J., 1996 ("Audesirk and Audesirk, 1996") [Teresa Audesirk and Gerald Audesirk]

Beers, M. H., and Berkow R., Editors, in the Publication on the World Wide Web (http://www.merck.com/pubs/mmanual/) entitled "The Merck Manual of Diagnosis and Therapy", "Seventeenth Edition", "Centennial Edition", Merck & Co., Whitehouse Station, N.J., 1999 (Beers, et al., 1999) [Mark H. Beers, M.D., and Robert Berkow, M.D.]

Balch, J. F., and Balch, P. A., in the book entitled "Prescription for Nutritional Healing", Second Edition, Avery Publishing Group, Garden City Park, New York, N.Y., 1997 ("Balch and Balch, 1997") [James F. Balch, M.D. and Phyllis A. Balch, C.N.C.]

Balch, J. F., and Balch, P. A., in the book entitled "Prescription for Nutritional Healing", Third Edition, Avery Publishing Group, Garden City Park, New York, N.Y., 2000 ("Balch and Balch, 2000") [James F. Balch, M.D. and Phyllis A. Balch, C.N.C.]

Buck, D. S., Nidorf, D. M., and Addino, J. G., in the article entitled "Comparison of two topical preparations for the treatment of onychomycosis: *Melaleuca Alternifolia* (tea tree) oil and clotrimazole", in the Journal of Family Practice, Volume 38, No. 6, pages 601–605, 1994 (Buck, et al., 1994")

Editor, article entitled "Protein could beat cholesterol as indicator of heart risk" in the section entitled "Medical Digest", The Seattle Times, Mar. 24, 2000, page A7 ("The Seattle Times, 2000")

Fugh-Berman, A., the book entitled "Alternative Medicine, What Works", Williams & Wilkins, Baltimore, Md., 1997 ("Fugh-Berman, 1997") [Adriane Fugh-Berman, M.D.]

Gunther, E., the book entitled "The Essential Oils", Volumes I, II, III, and IV, Lancaster Press, Lancaster, Pa., 1948

Hedges, L. M. and Wilkens, C. L., in the article entitled "Component Analysis of Eucalyptus Oil by Gas Chromatography-Fourier Transform-Infrared Spectrometry-Mass Spectrometry", in the publication called the Journal of Chromatographic Science, Volume 29, August, 1991 ("Hedges and Wilkens, 1991")

Igram, C., the book entitled "Killed on Contact, The Tea Tree Oil Story: Nature's Finest Antiseptic", Literary Visions Publishing, Inc., Cedar Rapids, Iowa, 1992 ("Igram, 1992") [Cass Igram, D.O.]

Jacobs, M. R., Hornfeldt, C. S., in the article entitled "Melaleuca oil poisoning", in the journal called "Clinical Toxicology", Volume 32, No. 4, pages 461–464, 1994 ("Jacobs and Hornfeldt, 1994")

Kohn, L., Corrigan, J., and Donaldson, M., Editors, the book entitled "To Err is Human, Building a Safer Health System", "Advanced Copy", Institute of Medicine, National Academy Press, Washington, D.C., 1999 (Kohn, et al., 1999) [Linda T. Kohn, Janet M. Corrigan, and Molla S. Donaldson]

Lawless, J., the book entitled "Tea Tree Oil", Harper Collins Publishers, Hammersmith, London, U.K., 1994 ("Lawless, 1994") [Julia Lawless]

Lawless, J., the book entitled "The Illustrated Encyclopedia of Essential Oils", Barnes & Noble Books, New York, N.Y., 1999 ("Lawless, 1999") [Julia Lawless]

Luckmann, J., Editor, the book entitled "Saunders, Manual of Nursing Care", W.B. Saunders Company, Philadelphia, Pa., 1997 ("Luckmann, 1997") [Joan Luckmann, MA, RN]

Martin, E., Ruse, M., and Holmes, E., Editors, the book entitled "A Dictionary of Biology", Third Edition, Oxford University Press, New York, N.Y., 1996 ("Martin, et al., 1996") [Elizabeth Martin MA; Michael Ruse BSc, PhD; and Elaine Holmes BSc, PhD]

Miller, L., and Miller, B., the book entitled "Ayurveda & Aromatherapy, The Earth Essential Guide to Ancient Wisdom and Modern Healing", *Lotus* Press, Twin Lakes, Wis., 1995 ("Miller and Miller, 1995") [Dr. Light Miller, ND, and Dr. Bryan Miller, DC]

Murray, M. T., in the book entitled "Natural Alternatives to Over-the-Counter and Prescription Drugs", William Morrow and Company, Inc., New York, N.Y., 1994, (Murray, 1994) [Michael T. Murray, N.D.]

Olsen, C., the book entitled "Australian Tea Tree Oil Guide", Kali Press, Pagosa Springs, Colo., 1991, ("Olsen, 1991") [Cynthia B. Olsen]

Olsen, C., the book entitled "Australian Tea Tree Oil Guide", Third Edition, Kali Press, Pagosa Springs, Colo., 1997 ("Olsen, 1997") [Cynthia Olsen]

Price, S., and Price, L., the book entitled "Aromatherapy for Health Professionals", Second Edition, Churchill Livingstone, New York, N.Y., 1999 (Price and Price, 1999) [Shirley Price and Len Price]

Rose, J., the book entitled "375 Essential Oils and Hydrosols", Frog, Limited, Berkeley, Calif., 1999 ("Rose, 1999") [Jeanne Rose]

Schnaubelt, K., the book entitled "Advanced Aromatherapy, The Science of Essential Oil Therapy", Healing Arts Press, a division of Inner Traditions International, Rochester, Vt., 1998 ("Schnaubelt, 1998") ["Kurt Schnaubelt, Ph.D."]

Sherry, E., and Warnke, P. H. H., the paper entitled "Alternative for MRSA and Tuberculosis (TB): Eucalyptus and Tea-Tree Oils as New Topical Antibacterials", Poster Board Number: P376, 2002 Annual Meeting of the American Academy of Orthopaedic Surgeons, Dallas, Tex., Feb. 13–17, 2002 (Sherry and Warnke, 2002) [Eugene Sherrry, M.D., and P. H. H. Warnke, Ph.D.]

Sullivan, J. B., Rummack, B. H., and Thomas, H., in the article entitled "Pennyroyal oil poising and hepatoxicity", in the Journal of the American Medical Association, Volume 242, No. 26, pages 2873–74, 1979 ("Sullivan, et al., 1979")

Swords, G. and Hunter, G. L. K., in the article entitled "Composition of Australian Tea Tree Oil (*Melaleuca alternifolia*)" presented in the Journal of Agricultural Food Chemistry, Volume 26, No. 3, 1978, pages 734–737 ("Swords and Hunter, 1978")

Vallence, W. B., the article entitled "Pennyroyal poisoning: a fatal case", in the journal called "Lancet", Volume 2, pages 850–851, 1955 ("Vallence, 1955")

Webb, N. J., and Pritt, W. R., in the article entitled "Eucalyptus oil poisoning in childhood: 41 cases in southeast Queensland", in the journal called "Journal of Paediatrics and Child Health", Volume 29, pages 368–371, 1993 ("Webb and Pritt, 1993")

Weinstein, A. M., the book entitled "Asmtha, The Complete Guide to Self-Management of Asthma and Allergies for Patients and Their Families", A Fawcett Crest Book, The Ballantine Publishing Group, New York, N.Y., 1988 ("Weinstein, 1988") [Allen M. Weinstein, M.D.]

Williams, D. G., in the article entitled "New Uses for An Age-Old Therapy", in the newsletter called "Alternatives For the Health Conscious Individual", Vol. 8, No. 4, October, 1999 ("Williams, 1999") [Dr. David G. Williams]

In addition, each above cited references refer to yet other papers, publications, books, etc., and entire copies of each and every such document is also incorporated herein by reference in their entirety. For example, Hedges and Wilkens, 1991, cite under its "References" and item "1." a book that is entitled "The Essential Oils", Vol. I, II, and IV, by the author of E. Gunther, Lancaster Press, Lancaster, Pa., 1948, and according the previous sentence, an entire copy of that reference is incorporated herein by this statement.

While the above description contains many specificities, these should not be construed as limitations on the scope of the invention, but rather as exemplification of preferred embodiments thereto. As have been briefly described, there are many possible variations. Accordingly, the scope of the invention should be determined not only by the embodiments illustrated, but by the appended claims and their legal equivalents.

What is claimed is:

1. A method to reduce the risks of infection of the human respiratory system by *Mycobacterium tuberculosis* in an enclosed public area having one or more human beings within said enclosed area comprising the following steps:

(a) within a period of time of 30 minutes before entering said public area, inhaling the concentrated vapors from a mixture of 50% of eucalyptus oil and 50% tea tree oil, whereby said concentrated vapors are generated within a hand-held atomizer apparatus, and whereby said concentrated vapors are inhaled through at least one orifice attached to said hand-held atomizer apparatus; and (b) after entering said public area, periodically inhaling the concentrated vapors from said mixture in said hand-held atomizer apparatus, whereby the period of time between successive inhalations exceeds 30 minutes, and whereby the period of time between successive inhalations is less than 2 hours;

and whereby infections from *Mycobacterium tuberculosis* are known to cause infections of the human respiratory system.

* * * * *